US006911474B2

(12) United States Patent
Piomelli et al.

(10) Patent No.: US 6,911,474 B2
(45) Date of Patent: Jun. 28, 2005

(54) METHODS, COMPOUNDS, AND COMPOSITIONS FOR REDUCING BODY FAT AND MODULATING FATTY ACID METABOLISM

(75) Inventors: Daniele Piomelli, Irvine, CA (US); Fernando Rodriguez de Fonseca, Madrid (ES)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 10/112,509

(22) Filed: Mar. 27, 2002

(65) Prior Publication Data

US 2003/0018081 A1 Jan. 23, 2003

Related U.S. Application Data

(60) Provisional application No. 60/336,289, filed on Oct. 31, 2001, and provisional application No. 60/279,542, filed on Mar. 27, 2001.

(51) Int. Cl.[7] .................. A61K 31/195; A61K 31/20
(52) U.S. Cl. ........................... 514/563; 514/558
(58) Field of Search ..................... 514/563, 558

(56) References Cited

U.S. PATENT DOCUMENTS

| | | | |
|---|---|---|---|
| 5,618,955 A | 4/1997 | Mechoulam et al. | |
| 5,631,297 A | 5/1997 | Pate et al. | |
| 5,679,667 A * | 10/1997 | Della Valle et al. | 514/182 |
| 5,847,008 A | 12/1998 | Doebber | |
| 5,859,051 A | 1/1999 | Adams | |
| 5,925,672 A | 7/1999 | Piomelli | |
| 5,962,012 A | 10/1999 | Lin | |
| 5,985,282 A * | 11/1999 | Haveson | 424/730 |
| 6,068,976 A | 5/2000 | Briggs et al. | |
| 6,090,836 A | 7/2000 | Adams | |
| 6,090,839 A | 7/2000 | Adams | |
| 6,096,784 A | 8/2000 | Lerner | |
| 6,160,000 A | 12/2000 | Adams | |
| 6,200,998 B1 | 3/2001 | Sahoo | |
| 6,261,595 B1 | 7/2001 | Stanley | |
| 6,271,015 B1 | 8/2001 | Gilula | |
| 6,274,608 B1 | 8/2001 | Sauerberg | |
| 6,344,474 B1 | 2/2002 | Maruani et al. | |
| 6,348,498 B1 | 2/2002 | Calignano | |
| 6,359,010 B1 | 3/2002 | Geracioti, Jr. et al. | |
| 2002/0035150 A1 | 3/2002 | Piomelli | |
| 2003/0041340 A1 * | 2/2003 | Cravatt | 800/15 |
| 2003/0149082 A1 | 8/2003 | Makriyannis et al. | |
| 2003/0195226 A1 | 10/2003 | Sit et al. | |

FOREIGN PATENT DOCUMENTS

| | | |
|---|---|---|
| WO | WO 94/12466 A1 | 6/1994 |
| WO | WO 97/27857 | 8/1997 |
| WO | WO 97/28149 | 8/1997 |
| WO | WO 97/36579 | 10/1997 |
| WO | WO 98/20119 | 5/1998 |
| WO | WO 98/24396 | 6/1998 |
| WO | WO 99/60987 A2 | 12/1999 |
| WO | WO 02/080903 A1 * | 10/2002 |

OTHER PUBLICATIONS

Calignano et al.; "Control of pain initiation by endogenous cannabinoids"; *Nature*; Jul. 16, 1998; vol. 394; pp. 277–281; Macmillan Publishers Ltd.
Piomelli et al.; "Structural determinants for recognition and translocation by the anandamide transporter"; *Proc. Natl. Acad. Sci. USA*; May 1999; vol. 96; pp. 5802–5807.
U.S. Appl. No. 10/642,462, filed Aug. 2003, Piomelli et al.
U.S. Appl. No. 60/485,062, filed Jul. 2003, Fu et al.
U.S. Appl. No. 10/681,858, filed Oct. 2003, Piomelli et al.
Auboeuf, D. et al., "Tissue distribution and quantification of the expression of mRNAs of peroxisome proliferators–activated receptors and liver X receptor–α in humans" *Diabetes* 46:1319–1327 (1997).
Ahern, G. P. "Activation of TRPV1 by the satiety factor oleoylethanolamide" *J. Biological Chemistry* 278(33):30429–30434 (Aug. 15, 2003).
Calignano, A. et al., "Antinociceptive activity of the endogenous fatty acid amide, palmitylethanolamide" *Eur. J. Pharmacol*, 419(2–3):191–8 (2001).
Desvergne, B. et al., "Peroxisome proliferators–activated receptors: Nuclear control of metabolism" *Endocrine Rev*. 20(5):649–688 (1999).
Di Tomaso, E. et al., "Endogenous lipids that activate cannabinoid receptors. Formation and inactivation" *Adv. Exp. Med. Biol.* 407:335–40 (1997).
Fu, J. et al., "Oleylethanolamide regulates feeding and body weight through activation of the nuclear receptor PPAR–alpha" *Nature* 425(6953):90–3 (2003).
Gaetani, S. et al., "Modulation of meal pattern in the rat by the anorexic lipid mediator oleoylethanolamide" *Neuropsychopharm.* 28(7):1311–6 (2003).
Gomez, R. et al., "A peripheral mechanism for CB1 cannabinoid receptor–dependent modulation of feeding" *J. Neurosci*, 22(21):9612–7 (2002).
Kersten, S. et al., "Roles of PPARs in health and disease" *Nature* 405:421–424 (2000).
Kliewer, S. et al., "Peroxisome proliferators–activated receptors: from genes to physiology" *Recent Prog Horm Res* 56:239–63 (2001).
Loviscach, M. et al., "Distribution of peroxisome proliferators–activated receptors (PPARs) in human skeletal muscle and adipose tissue: relation to insulin action" *Diabetologia* 43(3):304–11 (2000).

(Continued)

*Primary Examiner*—Shengjun Wang
*Assistant Examiner*—Jennifer Kim
(74) *Attorney, Agent, or Firm*—Townsend and Townsend and Crew LLP

(57) ABSTRACT

Methods, pharmaceutical compositions, and compounds for reducing body weight, modulating body lipid metabolism, and reducing food intake in mammals are provided. The compounds of the invention include fatty acid ethanolamide compounds, homologues and analogs of which the prototype is the endogenous fatty acid ethanolamide, oleoylethanolamide.

34 Claims, 8 Drawing Sheets

U.S. PATENT DOCUMENTS

Mechoulam, R. et al., "A hunger for cannabinoids" *Nature* 410:763–765 (2001).

Memon, R. et al., "Up–regulation of peroxisome proliferators–activated receptors (PPAR–alpha) and PPAR–gamma messenger ribonucleic acid expression in the liver in murine obesity: troglitazone induces expression of PPAR–gamma–responsive adipose tissue–specific genes in the liver of obese diabetic mice" *Endocrinology* 141(11):4021–31 (2000).

Moya–Camarena, S. et al., "Conjugated linoleic acid activates peroxisome proliferators–activated receptor alpha and beta subtypes but does not induce hepatic peroxisome proliferation in Sprague–Dawley rats" *Biochim Biophys Acta* 1436(3):331–42 (1999).

Piomelli, D. et al., "The endocannabinoid system as a target for therapeutic drugs" *Trends Pharmacol Sci.* 21(6):218–24 (2000).

Raloff, J. "Science News Online– Food for Thought: 'Prescription–strength chocolate'" at <http://www.sciencenews.org/sn_arch/10_12_96/food.htm> (Visited Sep. 10, 2003).

Regents of the University of California, "Natural, marijuana–like chemical may provide treatment for obesity– Study in Nature shows reduced feeding, weight gain" at <http://www.ucihealth.com/News/Releases/obesity_marijuana.htm> Nov. 7, 2001.

Schoonjans, K. et al., "The peroxisome proliferators activated receptors (PPARS) and their effects on lipid metabolism and adipocyte differentiation" *Biochim Biophys Acta* 1302 (2):93–109 (1996).

Stella, N. et al., "Receptor–dependent formation of endogenous cannabinoids in cortical neurons" *Eur. J. Pharmacol.* 425(3):189–96 (2001).

Tomaso, E. et al., "Brain cannabinoids in chocolate" *Nature* 382(Aug. 22):677 (1996).

H.O. Schmid, et al., "The N–acylation–phosphodiesterase pathway and cell signalling," *Chem. Phys. Lipids*, (1996), vol. 80, pp. 133–142.

K.D. Chapman, "Emerging physiological roles for N–acylphosphatidylethanolamine metabolism in plants: signal transduction and membrane protection," *Chem. Phys. Lipids*, (2000), vol. 108:22, pp. 221–229.

V. D. Marzo, et al., "Formation and inactivation of endogenous cannabinoid anandamide in central neurons," *Nature*, (1994), vol. 372, pp. 686–691.

A. Giuffrida, et al., "Dopamine activation of endogenous cannabinoid signaling in dorsal striatum," *Nat. Neurosci.*, (1999), vol. 2, No. 4, pp. 358–363.

E. Berdyshev, et al., "Stress–induced generation of IN–acylethanolamines in mouse epidermal JB6 P+ cells," *Biochem, J.*, (2000), vol. 346, pp. 369–374.

H. Cades, et al., "Biosynthesis of an Endogenous Cannabinoid Precursor in Neurons and its Control by Calcium and cAMP," *J. NeuroSci.*, (1996), vol. 16, pp. 3934–3942.

W. A. Devane, et al., "Isolation and Structure of a Brain Constituent That Binds to the Cannabinoid Receptor," *Science*, (1992), vol. 258, pp. 1946–1949.

G. Griffin, et al., "Cloning and Pharmacological Characterization of the Rat $CB_2$ Cannabinoid Receptor," *J. Pharmacol. Exp. Ther.*, (2000), vol. 292, No. 3, pp. 886–894.

A. Calignano, et al., "Control of pain initiation by endogenous cannabinoids," *Nature*, (1998), vol. 394, pp. 277–281.

B. M. Forman, et al., "Hypolipidemic drugs, polyunsaturated fatty acids, and eicosanoids are ligands for peroxisome proliferators–activated receptors α and δ," *PNAS*, (1997), vol. 94, pp. 4312–4317.

F. Desamaud, et al., "Anandamide Amidohydrolase Activity in Rat Brain Microsomes," *J. Biol. Chem.*, (1995), vol. 270, No. 11, pp. 6030–6035.

A. Giuffrida and D. Piomelli, "Purification and High–Resolution Analysis of Anandamide and Other Fatty Acylethanolamides," in S. G. Laychock, ed. and R. P. Rubin, ed. *Lipid Second Messengers*, CRC Press LLC, Boca Raton, Florida, (1999), pp. 113–133.

A. Giuffrida, et al., "Quantification of Bioactive Acylethanolamides in Rat Plasma by Electrospray Mass Spectrometry," *Anal. Biochem.*, (2000), vol. 280, pp. 87–93.

A. Calignano, et al., "Bidirectional control of airway responsiveness by endogenous cannabinoids," *Nature*, (2000), vol. 408, pp. 96–101.

D. Piomelli, et al., "Endogenous Cannabinoid Signaling," *Neurobiol. Dis.*, (1998), vol. 5, pp. 462–473 (1998).

H. Cadas, et al., "Occurrence and Biosynthesis of Endogenous Cannabinoid Precursor, N–Arachidonoyl Phosphatidylethanolamine, in Rat Brain," *J. Neurosci.*, (1997), vol. 17, No. 4, pp. 1226–1242.

N. R. Bachur, et al., "Fatty Acid Amides of Ethanolamine in Mammalian Tissues," *J. Biol. Chem.*, (1965), vol. 240, No. 3, pp. 1019–1024.

P. C. Schmid, et al., "Properties of Rat Liver N–Acylethanolamine Amidohydrolase," *J. Biol. Chem.*, (1985), vol. 260, No. 26, pp. 14145–14149.

A. Khanolkar, et al., "Structure–Activity Relationships of Anandamide, and Endogenous Cannabinoid Ligand," *Life Sci.*, (1999), vol. 65, No. 6/7, pp. 607–616.

D. L. Boger, et al., "Exceptionally potent inhibitors of fatty acid amide hydrolase: The enzyme responsible for degradation of endogenous oleamide and anandamide," *PNAS*, (2000), vol. 97, No. 10, pp. 5044–5049.

S. Conti, et al., "Antiinflammatory action of endocannabinoid palmitoylethanolamide and the synthetic cannabinoid nabilone in a model of acute inflammation in the rat," *British Journal of Pharmacology*, (2002), vol. 135, pp. 181–187.

B. F. Cravatt, et al., "Supersensitivity to anandamide and enhanced endogenous cannabinoid signaling inmice lacking fatty acid amide hydrolase," *PNAS*, (2001), vol. 98, No. 16, pp. 9371–9376.

F. Rodriguez de Fonseca, et al., "An anorexic lipid mediator regulated by feeding," *Nature*, (2001) vol. 414, pp. 209–212.

A. Giuffrida, et al., "Mechanisms of Endocannabinoid Inactivation: Biochemistry and Pharmacology," *J. Pharmacol. Exp. Ther.*, (2001), vol. 298, No. 1, pp. 7–14.

A. Giuffrida, et al., "Isotope dilution GC/MS determination of anandamide and other fatty acylethanolamides in rat blood plasma," *FEBS Letters*, (1998), vol. 422, pp. 373–376.

G. B. Quistad, et al., "Fatty Acid Amide Hydrolase Inhibition by Neurotoxic Organophosphorus Pesticides," *Toxicology and Applied Pharmacology*, (2001), vol. 173, pp. 48–55.

G. B. Quistad, et al., "Selective Inhibitors of Fatty Acid Amide Hydrolase Relative to Neuropathy Target Esterase and Acetylcholinesterase: Toxicological Implications," *Toxicology and Applied Pharmacology*, (2002), vol. 179, pp. 57–63.

T. M. Willson, et al., "The PPARs: From Orphan Receptors to Drug Discovery," *Journal of Medicinal Chemistry*, (2000), vol. 43, No. 4, pp. 527–550.

* cited by examiner

METHODS, COMPOUNDS, AND COMPOSITIONS FOR REDUCING BODY FAT AND MODULATING FATTY ACID METABOLISM

CROSS-REFERENCE TO RELATED APPLICATIONS

This application claims priority of U.S. Patent Application No. 60/336,289 filed Oct. 31, 2001 and U.S. Patent Application 60/279,542 filed Mar. 27, 2001. The contents of which are each incorporated herein by reference.

STATEMENT AS TO RIGHTS TO INVENTIONS MADE UNDER FEDERALLY SPONSORED RESEARCH AND DEVELOPMENT

This invention was made with government support under Grant No. DA 12653, awarded by the National Institute of Health. The Government has certain rights in this invention.

FIELD OF THE INVENTION

This invention relates to fatty acid ethanolamides, their homologues, and their analogs and to their use as pharmacologically active agents to reduce body fat, reduce food consumption, and modulate lipid metabolism.

BACKGROUND OF THE INVENTION

Obesity is a worldwide health challenge occuring at alarming levels in the United States and other developed nations. About 97 million adults in the United States are overweight. Of these 40 million are obese. Obesity and overweight greatly increase the risk of many diseases. Hypertension; type 2 diabetes; dyslipidemia; coronary heart disease; stroke; gallbladder disease; osteoarthritis; sleep apnea and other respiratory problems; and endometrial, breast, prostate, and colon cancers have been associated with higher body weights. Persons with higher body weights also suffer from a higher all-cause death rate. According to the National Institutes of Health about 280,000 adult deaths in the United States each year may be attributed in part to obesity.

Weight loss is desirable in the case of obesity and overweight individuals. Weight loss can help to prevent many of these harmful consequences, particularly with respect to diabetes and cardiovascular disease (CVD). Weight loss may also reduce blood pressure in both overweight hypertensive and non-hypertensive individuals; serum triglycerides levels and increases the beneficial high-density lipoprotein (HDL)-form of cholesterol. Weight loss also generally reduces somewhat the total serum cholesterol and low-density lipoprotein (LDL)-cholesterol levels. Weight loss may also reduce blood glucose levels in overweight and obese persons.

While weight loss is desirable, it is hard to achieve. Many treatments for the management of overweight and obesity and the maintenance of weight loss exist. However, recidivism is rampant. Approximately, 40 percent of women and 24 percent of men are trying to actively lose weight at any given time. These treatments include low-calorie diets and low-fat diets; increased physical exercise; behavioral therapies directed toward reducing food intake, pharmacotherapy; surgery; and combinations of the above.

The pharmacopoea of weight loss is relatively bare. Drugs such as sibutramine, dexfenfluramine, orlistat, phenylpropanolamine, phenteramine, or fenfluramine can facilitate weight loss in obese adults when used for prolonged periods. In general, however, the safety of long-term administration of pharmaco-therapeutic weight loss agents is unknown. For instance, recently due to concerns about valvular heart disease observed in patients, fenfluramine and dexfenfluramine have been withdrawn from the market. In the face of the slim pharmacopoea and the high prevalence of obesity and overweight, there is a need for new pharmaceutical methods and compositions to promote and maintain weight loss.

Fatty acid ethanolamides (FAE) are unusual components of animal and plant lipids, and their concentrations in non-stimulated cells are generally low (Bachur et al., *J. Biol. Chem.*, 240:1019–1024 (1965); Schmid et al., *Chem. Phys. Lipids*, 80:133–142 (1996); Chapman, K. D., *Chem. Phys. Lipids*, 108:221–229 (2000)). FAE biosynthesis can be rapidly enhanced, however, in response to a wide variety of physiological and pathological stimuli, including exposure to fungal pathogens in tobacco cells (Chapman et al., *Plant Physiol.*, 116:1163–1168 (1998)), activation of neurotransmitter receptors in rat brain neurons (Di Marzo et al., *Nature*, 372:686–691 (1994); Giuffrida et al., *Nat. Neurosci.*, 2:358–363 (1999)) and exposure to metabolic stressors in mouse epidermal cells (Berdyshev et al., *Biochem. J.*, 346:369–374 (2000)). The mechanism underlying stimulus-dependent FAE generation in mammalian tissues is thought to involve two concerted biochemical reactions: cleavage of the membrane phospholipid, N-acyl phosphatidylethanolamine (NAPE), catalyzed by an unknown phospholipase D; and NAPE synthesis, catalyzed by a calcium ion- and cyclic AMP-regulated N-acyltransferase (NAT) activity (Di Marzo et al., *Nature*, 372:686–691 (1994); Cadas et al., *J. NeuroSci.*, 6:3934–3942 (1996); Cadas et al., H., *J. Neurosci.*, 17:1226–1242, (1997)).

The fact that both plant and animal cells release FAEs in a stimulus-dependent manner suggests that these compounds may play important roles in cell-to-cell communication. Further support for this idea comes from the discovery that the polyunsaturated FAE, anandamide (arachidonylethanolamide), is an endogenous ligand for cannabinoid receptors (Devane et al., *Science*, 258:1946–1949 (1992))—G protein-coupled receptors expressed in neurons and immune cells, which recognize the marijuana constituent $\Delta^9$-tetrahydrocannabinol ($\Delta^9$-THC) (for review, see reference (Pertwee, R. G., *Exp. Opin. Invest. Drugs*, 9:1553–1571 (2000)).

Two observations make it unlikely that other FAEs also participate in cannabinoid neurotransmission. The FAE family is comprised for the most part of saturated and monounsaturated species, such as palmitylethanolamide and oleoylethanolamide, which do not significantly interact with cannabinoid receptors (Devane et al., *Science*, 258:1946–1949 (1992); Griffin et al., *J. Pharmacol. Exp. Ther.*, 292:886–894. (2000)). Second, when the pharmacological properties of the FAEs have been investigated in some detail, as is the case with palmitylethanolamide, such properties have been found to differ from those of $\Delta^9$-THC and to be independent of activation of known cannabinoid receptor subtypes (Calignano et al., *Nature*, 394:277–281 (1998)). Thus, the biological significance of the FAEs remains elusive.

Oleoylethanolamide (OEA) is a natural analogue of the endogenous cannabinoid anandamide. Like anandamide, OEA is produced in cells in a stimulus-dependent manner and is rapidly eliminated by enzymatic hydrolysis, suggesting a role in cellular signaling. However, unlike anandamide, OEA does not activate cannabinoid receptors and its biological functions were here-to-fore essentially unknown.

There is a need for additional methods and agents to treat obesity and overweight as well as to maintain weight loss. The present invention meets this need by providing novel methods and pharmaceutical compositions related to our instant discovery that oleoylethanolamide (OEA) and other fatty acid ethanolamide compounds (e.g., palmitylethanolamide, elaidylethanolamide)) can reduce appetite, food intake, body weight, and body fat and alter fat metabolism.

SUMMARY OF THE INVENTION

The present invention provides compounds, compositions, and methods for reducing body fat and for treating or preventing obesity, and overweight in mammals and the diseases associated with these health conditions. In one aspect, the invention provides methods for reducing body fat or body weight and for treating or preventing obesity or overweight and for reducing food intake by administration of pharmaceutical compositions comprising a fatty acid alkanolamide compound, homologue, or analog in an amount sufficient to reduce body fat, body weight or prevent body fat or body weight gain. In other aspects, the invention is drawn to the fatty acid ethanolamide compounds, homologues, analogs; and their pharmaceutical compositions and such methods of use.

In other embodiments, the fatty acid moiety of the fatty acid alkanolamide or ethanolamide compound, homologue, or analog may be saturated or unsaturated, and if unsaturated may be monounsaturated or polyunsaturated.

In some embodiments, the fatty acid moiety of the fatty acid alkanolamide compound, homologue, or analog is a fatty acid selected from the group consisting of oleic acid, palmitic acid, elaidic acid, palmitoleic acid, linoleic acid, alpha-linolenic acid, and gamma-linolenic acid. In certain embodiments, the fatty acid moieties have from twelve to 20 carbon atoms.

Other embodiments are provided by varying the hydroxyalkylamide moiety of the fatty acid amide compound, homologue or analog. These embodiments include the introduction of a substituted or unsubstituted lower ($C_1$–$C_3$) alkyl group on the hydroxyl group of an alkanolamide or ethanolamide moiety so as to form the corresponding lower alkyl ether. In another embodiment, the hydroxy group of the alknaolamide or ethanolamide moiety is bound to a carboxylate group of a $C_2$ to $C_6$ substituted or unsubstituted alkyl carboxylic acid to form the corresponding ester of the fatty acid ethanolamide. Such embodiments include fatty acid alkanolamide and fatty acid ethanolamides in ester linkage to organic carboxylic acids such as acetic acid, propionic acid, and butanoic acid. In one embodiment, the fatty acid alkanolamide is oleoylalkanolamide. In a further embodiment, the fatty acid alkanolamide is oleoylethanolamide.

In still another embodiment, the fatty acid ethanolamide compound, homologue, or analog further comprises a substituted or unsubstituted lower alkyl ($C_1$–$C_3$) group covalently bound to the nitrogen atom of the fatty acid ethanolamide.

In another aspect, the invention provides a pharmaceutical composition comprising a pharmaceutically acceptable excipient and a compound, or its pharmaceutically acceptable salt, having the formula:

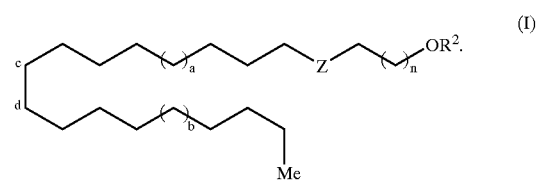

(I)

In this formula, n is from 0 to 5 and the sum of a and b can be from 0 to 4. Z is a member selected from —C(O)N(R°)—; —(R°)NC(O)—; —OC(O)—; —(O)CO—; O; NR°; and S, in which R° and $R^2$ are independently selected from the group consisting of unsubstituted or unsubstituted alkyl, hydrogen, substituted or unsubstituted $C_1$–$C_6$ alkyl, substituted or unsubstituted lower ($C_1$–$C_6$) acyl, homoalkyl, and aryl. Up to four hydrogen atoms of either or both the fatty acid portion and ethanolamine portion of the compound may also be substituted by methyl or a double bond. In addition, the molecular bond between carbons c and d may be unsaturated or saturated. In some embodiments, the fatty acid ethanolamide of the above formula is a naturally occurring compound.

In other aspects of the invention, the methods and compositions employ fatty acid ethanolamide and fatty acid alkanolamide compounds, homologs and analogs for reducing body weight in which the compounds, homologs and analogs cause weight loss when administered to test animals (e.g., rats, mice, rabbits, hamsters, guinea pigs).

In still other aspects, the invention is drawn to methods of using arylthiazolidinedione compounds and heteroaryl and aryl oxyacetic acid type compounds to reduce body fat, body weight and appetite.

Still other aspects of the invention address methods of using and administering the subject compounds and compositions for reducing body weight or reducing appetite or reducing food intake or causing hypophagia in mammals (e.g., humans, cats or dogs). The subject compositions may be administered by a variety of routes, including orally.

DETAILED DESCRIPTION OF THE INVENTION

Figure 1:
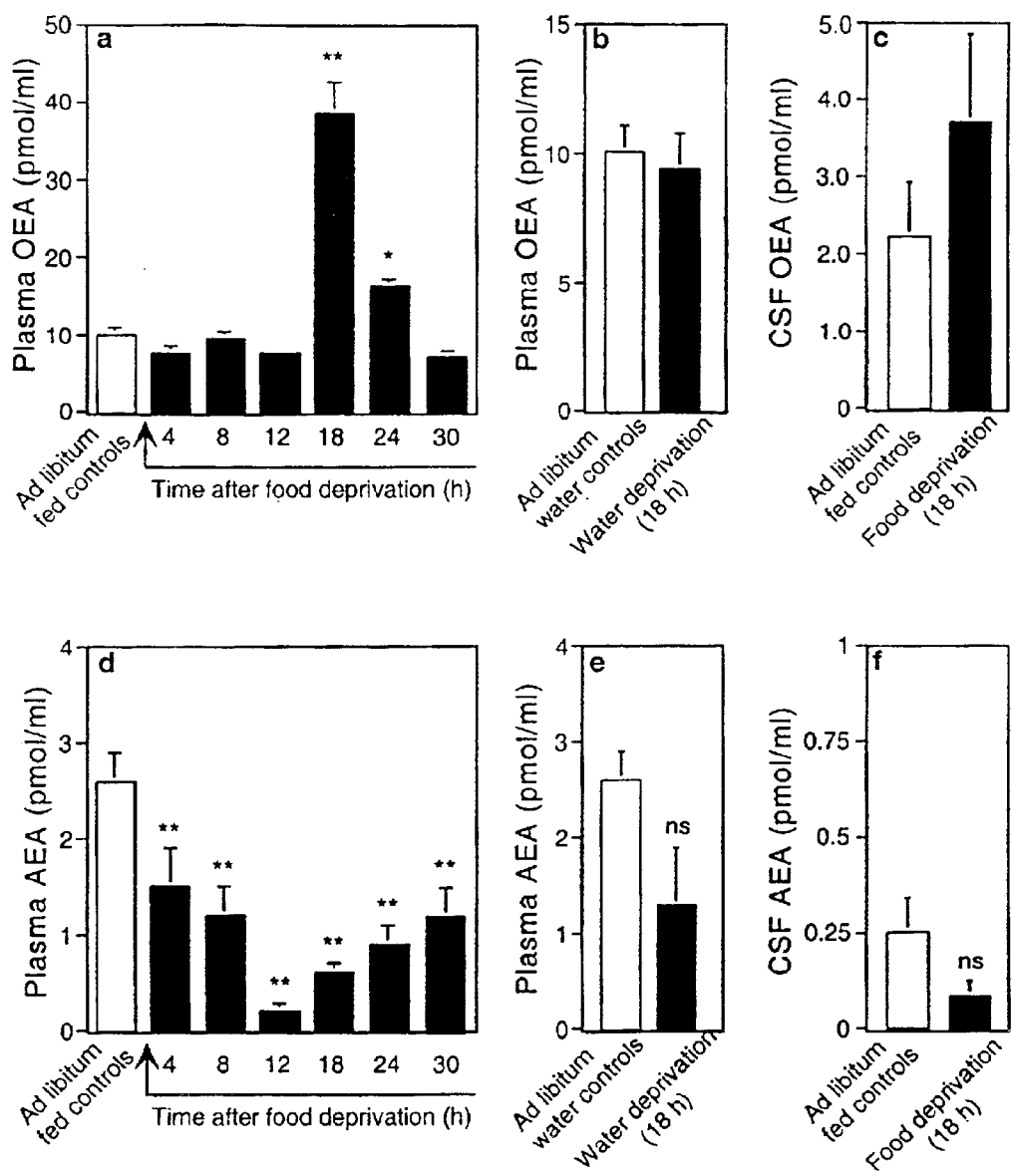
FIG. 1. Starvation increases circulating oleoylethanolamide levels in rats: (a) time course of the effects of food deprivation on plasma oleoylethanolamide (oleylethaolamide, OEA) levels; (b) effect of water deprivation (18 h) on plasma oleoylethanolamide levels; (c) effect of food deprivation (18 h) on oleoylethanolamide levels in cerebrospinal fluid (CSF); (d) time course of the effects of food deprivation on plasma anandamide (arachidonylethanolamide, ABA) levels; (e) effect of water deprivation (18 h) on anandamide plasma levels; (f) effect of food deprivation (18 h) on anandamide levels in CSF. Results are expressed as mean±s.e.m.; asterisk, $P<0.05$; two asterisks, $P<0.01$, $n=10$ per group.

This invention relates to the surprising discovery that OEA and other fatty acid alkanolamide compounds act to reduce food intake, body weight, and body fat and to modulate fatty acid oxidation. It has been surprisingly discovered that oleoylethanolamide (OEA), a natural lipid of heretofore unknown biological function in mammals, is a potent body fat reducing and weight control compound when administered to test animals. U.S. Patent Application No. 60/279,542, filed Mar. 27, 2001, and assigned to the same assignee and herein incorporated by reference in its entirety discloses OEA and OEA-like compounds as agents which can reduce body fat and appetite in mammals.

Upon the discovery of the prototype OEA, other fatty acid alkanolamide compounds and homologs were also found to be active.

OEA can serve as a model in the development of other fatty acid alkanolamide-like fat reducing compounds for treating obesity, inducing weight loss, reducing appetite, or food intake. This invention provides such other compounds as disclosed below.

The discovery that OEA adminstration acts to reduce appetite, food intake, and body weight can be used to identify other fatty acid ethanolamides, homologues, and analogs as weight and appetite control agents. This invention provides such agents.

DEFINITIONS

The abbreviations used herein have their conventional meaning within the chemical and biological arts.

Where substituent groups are specified by their conventional chemical formulae, written from left to right, they equally encompass the chemically identical substituents which would result from writing the structure from right to left, e.g., —CH₂O— is intended to also recite —OCH₂—.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. The term "pharmaceutical composition" indicates a composition suitable for pharmaceutical use in a subject, including an animal or human. A pharmaceutical composition generally comprises an effective amount of an active agent and a pharmaceutically acceptable carrier.

Compounds of the invention may contain one or more asymmetric centers and can thus occur as racemates and racemic mixtures, single enantiomers, diastereomeric mixtures and individual diastereomers. The present invention is meant to comprehend all such isomeric forms of the inventive compounds.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed by the inventive formulas.

Compounds of the invention include the diastereoisomers of pairs of enantiomers. Diastereomers for example, can be obtained by fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent.

Alternatively, any enantiomer of an inventive compound may be obtained by stereospecific synthesis using optically pure starting materials or reagents of known configuration As used herein, the term "heteroatom" is meant to include oxygen (O), nitrogen (N), sulfur (S) and silicon (Si).

"Alkanol," as used herein refers to a saturated or unsaturated, substituted or unsubstituted, branched or unbranched alkyl group having a hydroxyl substituent, or a substituent derivable from a hydroxyl moiety, e.g, ether, ester. The alkanol is preferably also substituted with a nitrogen-, sulfur-, or oxygen-bearing substituent that is included in bond Z (Formula I), between the "fatty acid" and the alkanol.

"Fatty acid," as used herein, refers to a saturated or unsaturated substituted or unsubstituted, branched or unbranched alkyl group having a carboxyl substituent. Preferred fatty acids are $C_4$–$C_{22}$ acids. Fatty acid also encompasses species in which the carboxyl substituent is replaced with a —$CH_2$— moiety.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$–$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups which are limited to hydrocarbon groups are termed "homoalkyl".

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—$CH_3$, —CH=CH—O—$CH_3$, —Si($CH_3$)$_3$, —$CH_2$—CH=N—$OCH_3$, and —CH=CH—N ($CH_3$)—$CH_3$. Up to two heteroatoms may be consecutive, such as, for example, —$CH_2$—NH—$OCH_3$ and —$CH_2$—O—Si ($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo ($C_1$–$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1–3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: halogen, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro(C$_1$–C$_4$)alkoxy, and fluoro(C$_1$–C$_4$)alkyl, in a number ranging from zero to the total number of open valences on the aromatic ring system; and where R', R", R'" and R"" are preferably independently selected from hydrogen, (C$_1$–C$_8$) alkyl and heteroalkyl, unsubstituted aryl and heteroaryl, (unsubstituted aryl)-(C$_1$–C$_4$)alkyl, and (unsubstituted aryl) oxy-(C$_1$–C$_4$)alkyl. When a compound of the invention includes more than one R group, for example, each of the R groups is independently selected as are each R', R", R'" and R"" groups when more than one of these groups is present.

The term "body fat reduction" means loss of a portion of body fat.

The formula for Body Mass Index (BMI) is [Weight in pounds÷Height in inches÷Height in inches]×703. BMI cutpoints for human adults are one fixed number, regardless of age or sex, using the following guidelines: Overweight human adults individuals have a BMI of 25.0 to 29.9. Obese human adults have a BMI of 30.0 or more. Underweight adults have a BMI less of than 18.5. A nomal body weight range for an adult is defined as a BMI between 18.5 and 25. BMI cutpoints for children under 16 are defined according to percentiles: Overweight is defined as a BMI for age greater than ≧85th percentile and obesity is defined as a BMI-for-age ≧95th percentile. Underweight is a BMI-for-age <5th percentile. A normal body weight range for a child is defined as a BMI above the 5th percentile and below the 85 percentile.

The term "fatty acid oxidation" relates to the conversion of fatty acids (e.g., oleate) into ketone bodies.

The term "hepatocytes" refers to cells originally derived from liver tissue. Hepatocytes may be freshly isolated from liver tissue or established cell lines.

The term "modulate" means to induce any change including increasing or decreasing. (e.g., a modulator of fatty acid oxidation increases or decreases the rate of fatty oxidation.

The term "muscle cells" refers to cells derived from the predominant cells of muscle tissue. Muscle cells may be freshly isolated from muscle tissue or established cell lines.

The term "obese" indicates a body weight 20% over ideal body weight as measured by body mass index Oleoylethanolamide (OEA) refers to a natural lipid of the following structure:

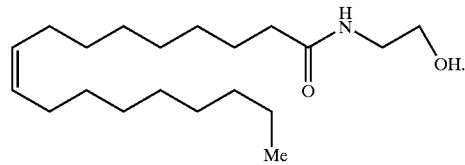

In the formulas herein, "Me" represents the methyl group.

The term "weight loss" refers to loss of a portion of total body weight.

The term "pharmaceutically acceptable carrier" encompasses any of the standard pharmaceutical carriers, buffers and excipients, including phosphate-buffered saline solution, water, and emulsions (such as an oil/water or water/oil emulsion), and various types of wetting agents and/or adjuvants. Suitable pharmaceutical carriers and their formulations are described in REMINGTON'S PHARMACEUTICAL SCIENCES (Mack Publishing Co., Easton, 19th ed. 1995). Preferred pharmaceutical carriers depend upon the intended mode of administration of the active agent. Typical modes of administration are described below.

The term "effective amount" means a dosage sufficient to produce a desired result. The desired result may comprise a subjective or objective improvement in the recipient of the dosage. A subjective improvement may be decreased appetite or craving for food. An objective improvement may be decreased body weight, body fat, or food, decreased food consumption, or decreased food seeking behavior.

A "prophylactic treatment" is a treatment administered to a subject who does not exhibit signs of a disease or exhibits only early signs of a disease, wherein treatment is administered for the purpose of decreasing the risk of developing a pathology associated with increased body weight or body fat. The compounds of the invention may be given as a prophylactic treatment to prevent undesirable or unwanted weight gain.

A "therapeutic treatment" is a treatment administered to a subject who exhibits signs of pathology, wherein treatment is administered for the purpose of diminishing or eliminating those pathological signs.

The term "to control weight" encompasses the loss of body mass or the reduction of weight gain over time.

The methods, compounds and compositions of the present invention are generally useful for reducing or controlling body fat and body weight in mammals. For instance, the methods, compositions, and compounds of the present invention are helpful in reducing appetite or inducing hypophagia in mammals. The methods, compounds, and compositions are also useful in preventing or mitigating the diseases associated with overweight or obesity by promoting the loss of body fat and body weight.

The methods, compositions, and compounds of the present invention include modulators of lipid metabolism, and particularly, fat and fatty acid catabolism.

Compounds of the Invention

Certain compounds of the present invention may possess asymmetric carbon atoms (optical centers) or double bonds; the racemates, diastereomers, geometric isomers and individual isomers are all intended to be encompassed within the scope of the present invention.

Such compounds of the invention may be separated into diastereoisomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent.

Alternatively, any enantiomer of such a compound of the invention may be obtained by stereospecific synthesis using optically pure starting materials of known configuration.

The compounds of the present invention may have unnatural ratios of atomic isotopes at one or more of their atoms. For example, the compounds may be radiolabeled with isotopes, such as tritium or carbon-14. All isotopic variations of the compounds of the present invention, whether radioactive or not, are within the scope of the present invention.

The instant compounds may be isolated in the form of their pharmaceutically acceptable acid addition salts, such as the salts derived from using inorganic and organic acids. Such acids may include hydrochloric, nitric, sulfuric, phosphoric, formic, acetic, trifluoroacetic, propionic, maleic, succinic, malonic and the like. In addition, certain compounds containing an acidic function can be in the form of their inorganic salt in which the counterion can be selected from sodium, potassium, lithium, calcium, magnesium and the like, as well as from organic bases. The term "pharmaceutically acceptable salts" refers to salts prepared from pharmaceutically acceptable non-toxic bases or acids including inorganic bases or acids and organic bases or acids.

The invention also encompasses prodrugs of the present compounds, which on administration undergo chemical conversion by metabolic processes before becoming active pharmacological substances. In general, such prodrugs will be derivatives of the present compounds that are readily convertible in vivo into a functional compound of the invention. Conventional procedures for the selection and preparation of suitable prodrug derivatives are described, for example, in "Design of Prodrugs", ed. H. Bundgaard, Elsevier, 1985. The invention also encompasses active metabolites of the present compounds.

A. Fatty Acid Alkanolamide Compounds, Homologs, and Analogs.

Compounds of the invention include body fat reducing fatty acid alkanolamide compounds, including the fatty acid ethanolamide compounds, and their homologues and certain analogs of the fatty acid alkanolamides. Such compounds may be identified and defined in terms of either an ability to cause reduced appetite, food intake, and/or body weight or body fat upon administration to test animals in vivo.

A variety of such fatty acid alkanolamides, homologs and analogs are therefore contemplated. Compounds of the invention include compounds of the following general formula:

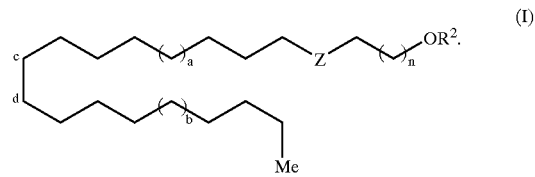

(I)

In this formula, n is from 0 to 5 and the sum of a and b can be from 0 to 4. Z is a member selected from —C(O)N(R°)—; —(R°)NC(O)—; —OC(O)—; —(O)CO—; O; NR°; and S, in which R° and $R^2$ are independently selected from the group consisting of unsubstituted or unsubstituted alkyl, hydrogen, substituted or unsubstituted $C_1$–$C_6$ alkyl, substituted or unsubstituted lower ($C_1$–$C_6$) acyl, homoalkyl, and aryl. Up to four hydrogen atoms of either or both the fatty acid portion and alkanolamine (e.g. ethanolamine) portion of the compound may also be substituted by methyl or a double bond. In addition, the molecular bond between carbons c and d may be unsaturated or saturated. In some embodiments, the fatty acid ethanolamide of the above formula is a naturally occurring compound.

Compounds of the invention also include compounds of the following formula:

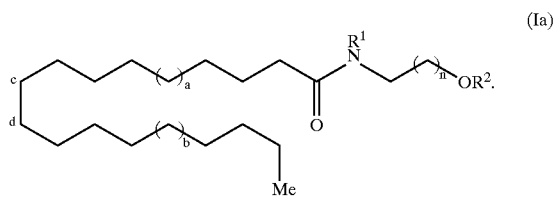

(Ia)

In one embodiment, the compounds of Formula Ia have n from 0 to 5; and a sum of a and b that is from 0 to 4; and members $R^1$ and $R^2$ independently selected from the group consisting of hydrogen, substituted or unsubstituted $C_1$–$C_6$ alkyl, lower substituted or unsubstituted ($C_1$–$C_6$) acyl, homoalkyl, and substituted or unsubstituted aryl. In this embodiment, up to four hydrogen atoms of the fatty acid portion and alkanolamine (e.g., ethanolamine) portion of compounds of the above formula may also be substituted by methyl or a double bond. In addition, the molecular bond between carbons c and d may be unsaturated or saturated. In some embodiments with acyl groups, the acyl groups may be the propionic, acetic, or butyric acids and attached via an ester linkage as $R^2$ or an amide linkage as $R^1$.

In another embodiment, the above compounds particularly include those in which the fatty acid moiety comprises oleic acid, elaidic acid, or palmitic acid. Such compounds include oleoylethanolamide, elaidylethanolamide and palmitylethanolamide.

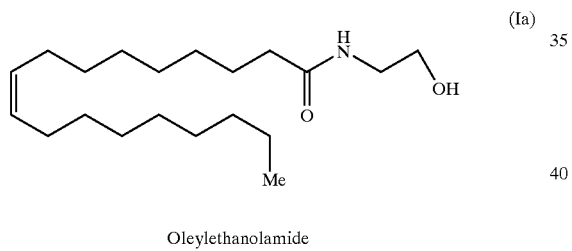

(Ia)

Oleylethanolamide

In another embodiment, the compounds of Formula Ia have n from 1 to 3; and a sum of a and b that is from 1 to 3; and members $R^1$ and $R^2$ independently selected from the group consisting of hydrogen, substituted or unsubstituted $C_1$–$C_6$ alkyl, and lower substituted or unsubstituted ($C_1$–$C_6$) acyl. In this embodiment, up to four hydrogen atoms of the fatty acid portion and alkanolamine (e.g., ethanolamine) portion of compounds of the above formula may also be substituted by methyl or a double bond. In addition, the molecular bond between carbons c and d may be unsaturated or saturated. In a further embodiment, the molecular bond between carbons c and d is unsaturated and no other hydrogen atoms are substituted. In a still further embodiment thereof, the members $R^1$ and $R^2$ are independently selected from the group consisting of hydrogen, substituted or unsubstituted $C_1$–$C_3$ alkyl, and substituted or unsubstituted lower ($C_1$–$C_3$) acyl.

Exemplary compounds provide mono-methyl substituted compounds, including ethanolamides, of Formula Ia. Such compounds include:

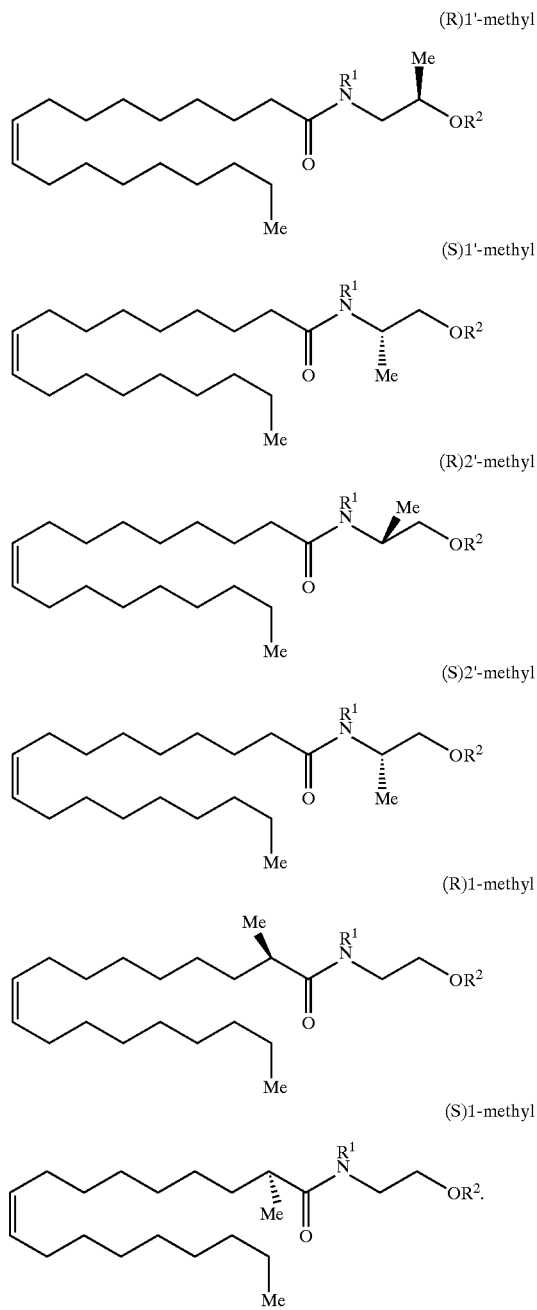

The methyl substituted compounds of the above formula include particularly those compounds where $R^1$ and $R^2$ are both H: (R)1'-methyloleoylethanolamide, S(1')-methyloleoylethanolamide, (R)2'-methyloleoylethanolamide, (S)2'-methyloleoylethanolamide, (R)1-methyloleoylethanolamide, and (S)1-methyloleoylethanolamide.

Reverse OEA-Like Compounds.

Compounds of the invention also include a variety of analogs of OEA. These compounds include reverse OEA compounds of the general formula:

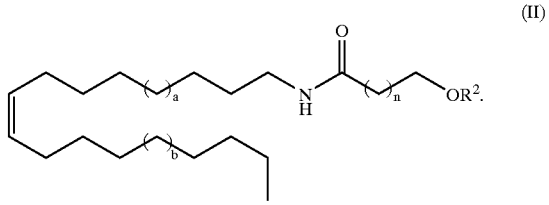

(II)

In some embodiments, the invention provides compounds of Formula II. Exemplary the compounds of Formula II have n from 1 to 5, and a sum of a and b from 0 to 4. In this embodiment, the member $R^2$ is selected from the group consisting of hydrogen, substituted or unsubstituted $C_1$–$C_6$ alkyl, substituted or unsubstituted lower ($C_1$–$C_6$) acyl, homoalkyl, and aryl. In addition, up to four hydrogen atoms of either or both the fatty acid portion and alkanolamine (e.g., ethanolamine) portion of compounds of the above formula may also be substituted by methyl or a double bond.

Exemplary compounds of formula II include those compounds where the alkanolamine portion is ethanolamine, compounds where $R^2$ is H, and compounds where a and b are each 1, and compounds where n is 1.

One embodiment of a compound according to Formula II is

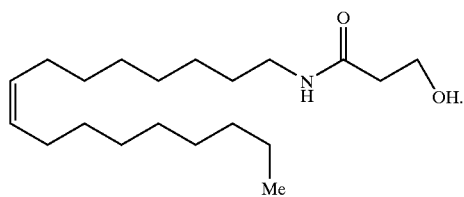

Reverse OEA

In another embodiment, the compounds of Formula II have n from 1 to 5 and a sum of a and b from 1 to 3. In this embodiment, the member $R^2$ is selected from the group consisting of hydrogen, substituted or unsubstituted $C_1$–$C_6$ alkyl, and substituted or unsubstituted lower ($C_1$–$C_6$) acyl. In addition, up to four hydrogen atoms of either or both the fatty acid portion and alkanolamine (e.g., ethanolamine) portion of compounds of the above formula may also be substituted by methyl or a double bond.

Oleoylalkanol Ester Compounds.

Compounds of the invention also include oleoylalkanol esters of the general formula:

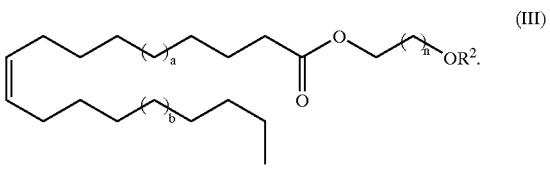

(III)

In some embodiments, the compounds of Formula III, have n from 1 to 5; and the sum of a and b from 0 to 4. The member $R^2$ is selected from the group consisting of hydrogen, substituted or unsubstituted $C_1$–$C_6$ alkyl, lower ($C_1$–$C_6$) acyl, homoalkyl, and aryl. Up to four hydrogen atoms of either or both the fatty acid portion and alkanol (e.g., ethanol) portion of compounds of the above formula may also be substituted by methyl or a double bond.

In some embodiments, the compounds of Formula III, have n from 1 to 3; and the sum of a and b from 1 to 3. The member $R^2$ is selected from the group consisting of hydrogen, substituted or unsubstituted $C_1$–$C_6$ alkyl, and substituted or unsubstituted lower ($C_1$–$C_6$) acyl. Up to four hydrogen atoms of the fatty acid portion and alkanol (e.g., ethanol) portion of compounds of the above formula may also be substituted by methyl or a double bond.

Compounds of Formula III include those compounds where $R^2$ is H, compounds where a and b are each 1, and compounds where n is 1. Examples of compounds according to Formula III include the oleoyldiethanol ester:

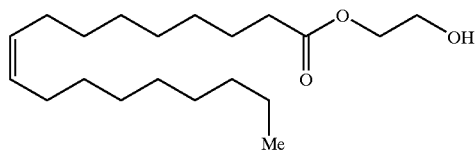

Compounds of Formula III also include mono-methyl substituted oleoyl ethanol esters such as the (R or S)-2'-methyloleoylethanolesters; the (R or S)-1'-methyloleoylethanolesters; and the (R or S))-1'-methyloleoylethanolesters; respectively:

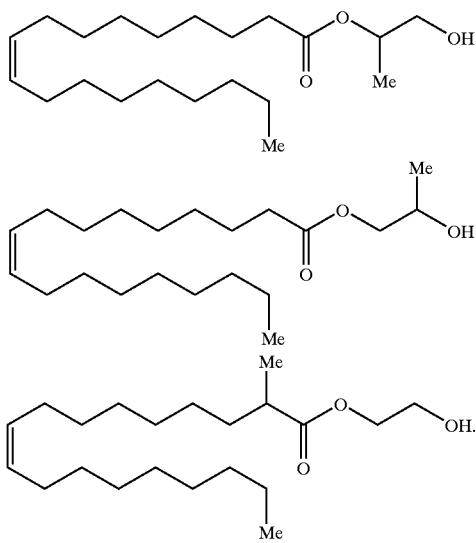

Oleoyl Alkanol Ethers

Compounds of the invention also include oleoylalkanol ethers according to the general formula:

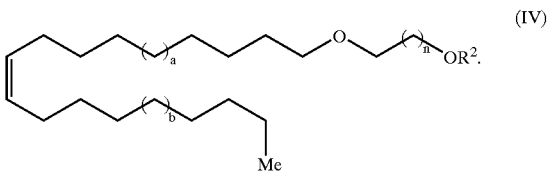

(IV)

In some embodiments, the compounds of Formula IV, have an n from 1 to 5 and a sum of a and b that can be from 0 to 4. The member $R^2$ is selected from the group consisting of hydrogen, substituted or unsubstituted $C_1$–$C_6$ alkyl, substituted or unsubstituted lower ($C_1$–$C_6$) acyl, alkyl, and substituted and unsubstituted aryl. Up to four hydrogen atoms of either or both the fatty acid portion and alkanol (e.g., ethanol) portion of compounds of the above formula may also be substituted by methyl or a double bond.

In other embodiments, the compounds of Formula IV, have n from 1 to 3; and the sum of a and b can be from 1 to 3. The member $R^2$ is selected from the group consisting of hydrogen, substituted or unsubstituted $C_1$–$C_6$ alkyl, and substituted or unsubstituted lower ($C_1$–$C_6$) acyl. Up to four hydrogen atoms of either or both the fatty acid portion and alkanol (e.g., ethanol) portion of compounds of the above formula may also be substituted by methyl or a double bond.

Compounds of Formula IV include those compounds where $R^2$ is H, compounds where a and b are each 1, and compounds where n is 1. Examples of compounds according to Formula IV include the following (R or S) 1'-oleoylethanol ethers and (R or S)-2'-oleoylethanol ethers:

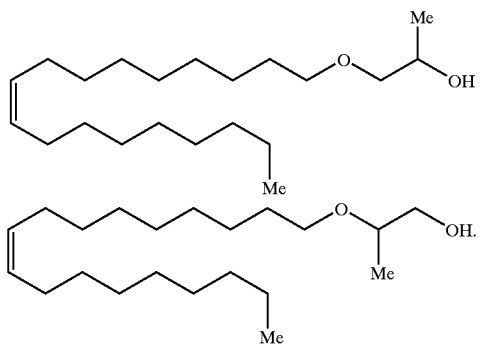

Fatty Acid Alkanolamide Analogs Having Polar Head Variants.

Compounds of the invention also include a variety of polar head analogs of OEA. These compounds include compounds having a fatty acid moiety of the general formula:

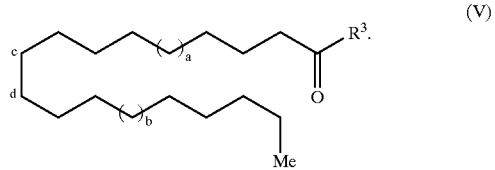

(V)

In some embodiments, the compounds of Formula V have a sum of a and b that can be from 0 to 4. In other embodiments, the sum of a and b is from 1 to 3. In these embodiments, up to four hydrogen atoms of the compounds of the above formula may also be substituted by methyl or a double bond. In addition, the molecular bond between carbons c and d may be unsaturated or saturated. A particularly preferred embodiment is that of the oleic acid fatty acid moiety:

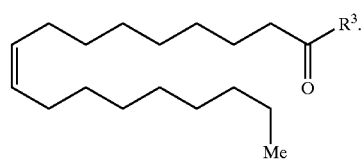

The $R^3$ group of the above structures may be selected from any of the following:

HO—$(CH_2)_z$—NH— wherein z is from 1 to 5, and the alkyl portion thereof is an unbranched methylene chain. For example:

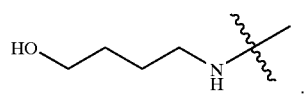

$H_2N$—$(CH_2)_z$—NH— wherein z is from 1 to 5, and the alkyl portion thereof is an unbranched methylene chain. For example:

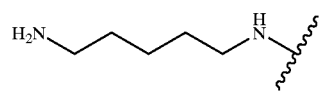

HO—$(CH_2)_x$—NH— wherein x is from 1 to 8, and the alkyl portion thereof may be branched or cyclic. For example,

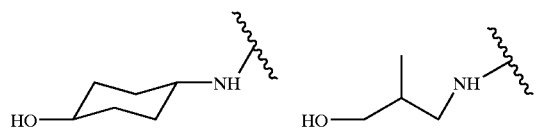

Additional polar head groups for $R^3$ include, for instance, compounds having furan, dihydrofuran and tetrahydrofuran functional groups:

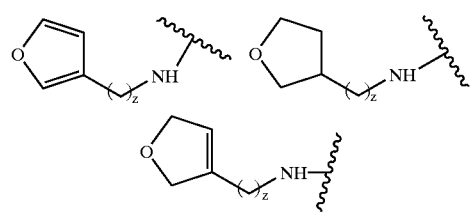

In the above structures, z can be from 1 to 5.

Compounds of the invention include, for instance, those having $R^3$ polar head groups based upon pyrole, pyrrolidine, and pyrroline rings:

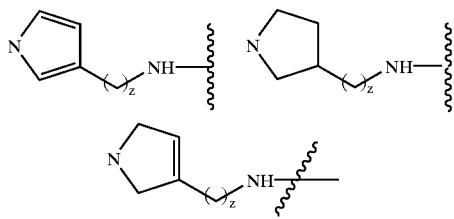

In the compounds of the above structures, z can be from 1 to 5.

Other exemplary polar head groups includea variety of imidazole and oxazoles, for example:

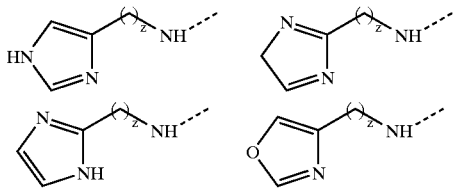

-continued

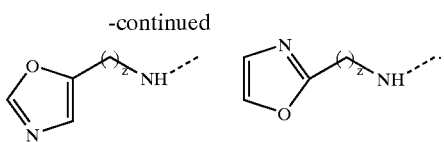

In the compounds of the above structures, z can be from 1 to 5.

Oxazolpyridine polar head groups are also exemplary:

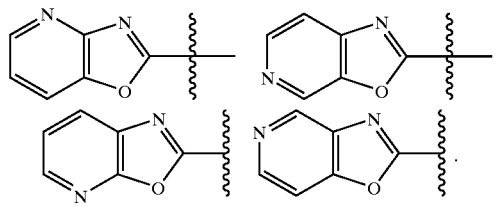

Fatty Acid Alkanolamide Analogs Having Apolar Tail Variants.

Compounds of the invention include a variety of alkanolamide and ethanolamide compounds having a variety of flexible apolar tails. These compounds include compounds of the following formulas in which R represents an ethanolamine moiety, an alkanolamine moiety, or a stable analog thereof. In the case of ethanolamine, the ethanolamine moiety is attached preferably via the ethanolamine nitrogen rather than the ethanolamine oxygen.

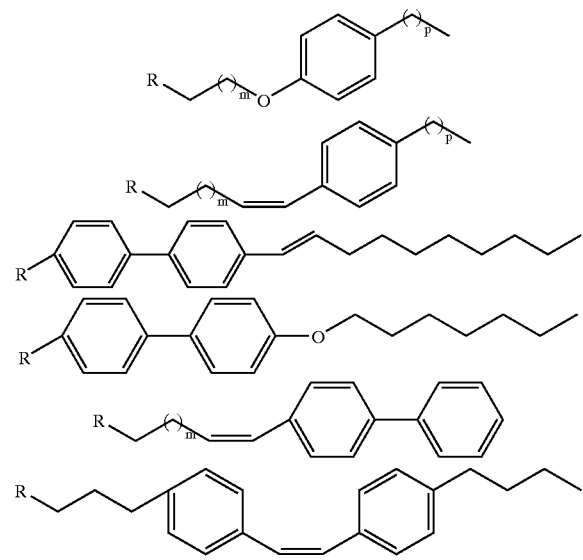

In the above structures, m is from 1 to 9 and p is independently from 1 to 5.

An exemplary compound is:

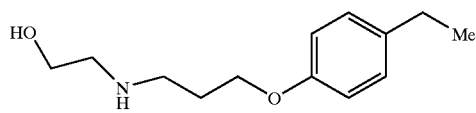

Another exemplary compound is an ethanolamine analog with an apolar tail of the following structural formula:

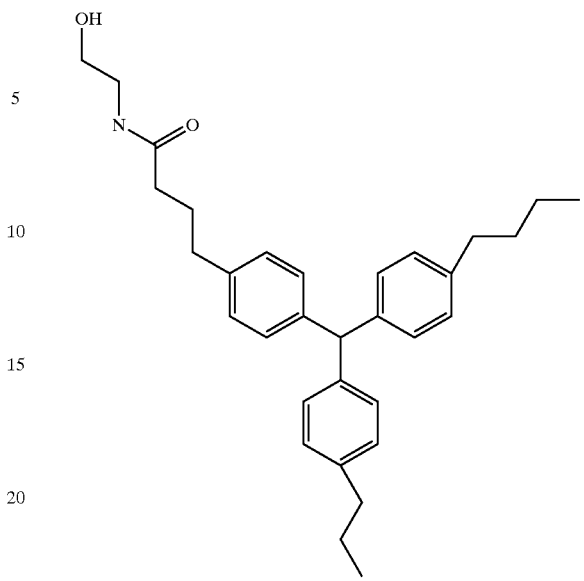

Exemplary compounds include analogs of fatty acid alkanolamides. Such analogs include those compounds taught in U.S. Pat. No. 6,200,998 (hereby incorporated by reference). This reference teaches compounds of the general formula:

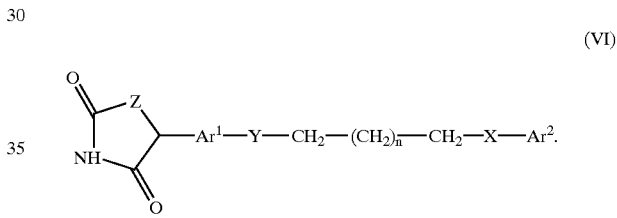

(VI)

In the above formula, and as defined in U.S. Pat. No. 6,200,998, $Ar^1$ is (1) arylene or (2) heteroarylene, wherein arylene and heteroarylene are optionally substituted with from 1 to 4 groups selected from $R^a$; $Ar^2$ is (1) ortho-substituted aryl or (2) ortho-substituted heteroaryl, wherein said ortho substituent is selected from R; and aryl and heteroaryl are optionally further substituted with from 1–4 groups independently selected from $R^a$; X and Y are independently O, S, N—$R^b$, or $CH_2$; Z is O or S; n is 0 to 3; R is (1) $C_{3-10}$ alkyl optionally substituted with 1–4 groups selected from halo and $C_{3-6}$ cycloalkyl, (2) $C_{3-10}$ alkenyl, or (3) $C_{3-8}$ cycloalkyl; $R^a$ is (1) $C_{1-15}$ alkanoyl, (2) $C_{1-15}$ alkyl, (3) $C_{2-15}$ alkenyl, (4) $C_{2-15}$ alkynyl, (5) halo, (6) $OR^b$, (7) aryl, or (8) heteroaryl, wherein said alkyl, alkenyl, alkynyl, and alkanoyl are optionally substituted with from 1–5 groups selected from $R^c$, and said aryl and heteroaryl optionally substituted with 1 to 5 groups selected from $R^d$; $R^b$ is (1) hydrogen, (2) $C_{1-10}$ alkyl, (3) $C_{2-10}$ alkenyl, (4) $C_{2-10}$ alkynyl, (5) aryl, (6) heteroaryl, (7) aryl $C_{1-15}$ alkyl, (8) heteroaryl $C_{1-15}$ alkyl, (9) $C_{1-15}$ alkanoyl, (10) $C_{3-8}$ cycloalkyl, wherein alkyl, alkenyl, alkynyl are optionally substituted with one to four substituents independently selected from $R^c$, and cycloalkyl, aryl and heteroaryl are optionally substituted with one to four substituents independently selected from $R^d$; or $R^c$ is (1) halo, (2) aryl, (3) heteroaryl, (4) CN, (5) $NO_2$, (6) $OR^f$; (7) $S(O)_mR^f$, m=0, 1 or 2;(8) $NR^fR^f$, (9) $NR^fCOR^f$, (10) $NR^fCO_2 R^f$, (11) $NR^fCON(R^f)_2$, (12) $NR^f SO_2 R^f$, provided that $R^f$ is not H, (13) $COR^f$, (14) $CO_2R^f$,

(15) CON($R^f$)$_2$, (16) SO$_2$ N($R^f$)$_2$, (17) OCON($R^f$)$_2$, or (18) C$_{3-8}$ cycloalkyl, wherein said cycloalkyl, aryl and heteroaryl are optionally substituted with 1 to 3 groups of halo or C$_{1-6}$ alkyl; $R^d$ is (1) a group selected from $R^e$, (2) C$_{1-10}$ alkyl, (3) C$_{2-10}$ alkenyl, (4) C$_{2-10}$ alkynyl, (5) aryl C$_{1-10}$ alkyl, or (6) heteroaryl C$_{1-10}$ alkyl, wherein alkyl, alkenyl, alkynyl, aryl, heteroaryl are optionally substituted with a group independently selected from $R^e$; $R^e$ is (1) halogen, (2) amino, (3) carboxy, (4) C$_{1-4}$ alkyl, (5) C$_{1-4}$ alkoxy, (6) hydroxy, (7) aryl, (8) aryl C$_{1-4}$ alkyl, or (9) aryloxy; $R^f$ is (1) hydrogen, (2) C$_{1-10}$ alkyl, (3) C$_{2-10}$ (3) C$_{2-10}$ alkenyl, (4) C$_{2-10}$ alkynyl, (5) aryl, (6) heteroaryl, (7) aryl C$_{1-15}$ alkyl, (8) heteroaryl C$_{1-15}$ alkyl, (9) C$_{1-15}$ alkanoyl, (10) C$_{3-8}$ cycloalkyl; wherein alkyl, alkenyl, alkynyl, aryl, heteroaryl, alkanoyl and cycloalkyl are optionally substituted with one to four groups selected from $R^e$.

Also preferred are the analogs taught in U.S. Pat. No. 5,859,051. These analogs have the following general formula:

(VII)

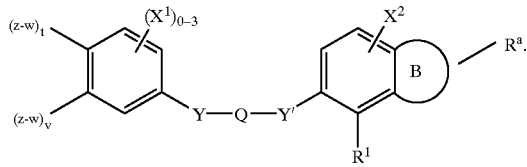

In the embodiments according to Formula VII, as defined in U.S. Pat. No. 5,859,051, $R^1$ is selected from the group consisting of H, C$_{1-6}$ alkyl, C$_{5-10}$ aryl, and C$_{5-10}$ heteroaryl, said alkyl, aryl and heteroaryl optionally substituted with 1 to 3 groups of $R^a$; $R^1$ is selected from a group consisting of: H, C$_{1-15}$ alkyl, C$_{2-15}$ alkenyl, C$_{2-15}$ alkynyl and C$_{3-10}$ cycloalkyl, said alkyl, alkenyl, alkynyl, and cycloalkyl optionally substituted with 1 to 3 groups of $R^a$; $R^3$ is selected from a group consisting of: H, NHR$^1$, NHacyl, C$_{1-15}$ alkyl, C$_{3-10}$ cycloalkyl, C$_{2-15}$ alkenyl, C$_{1-15}$ alkoxy, CO$_2$ alkyl, OH, C$_{2-15}$ alkynyl, C$_{5-10}$ aryl, C$_{5-10}$ heteroaryl said alkyl, cycloalkyl, alkenyl, alkynyl, aryl and heteroaryl optionally substituted with 1 to 3 groups of $R^a$; (Z-W—) is Z-CR$^6$R$^7$—, Z-CH.=CH—, or:

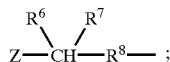

$R^8$ is selected from the group consisting of CR$^6$R$^7$, O, NR$^6$, and S(O)$_P$; $R^6$ and $R^7$ are independently selected from the group consisting of H, C$_{1-6}$ alkyl; B is selected from the group consisting of: 1) a 5 or 6 membered heterocycle containing 0 to 2 double bonds, and 1 heteroatom selected from the group consisting of O, S and N, heteroatom being substituted at any position on the five or six membered heterocycle, the heterocycle being optionally unsubstituted or substituted with 1 to 3 groups of $R^a$; 2) a 5 or 6 membered carbocycle containing 0 to 2 double bonds, the carbocycle optionally unsubstituted or substituted with 1 to 3 groups of $R^a$ at any position on the five or six membered carbocycle; and 3) a 5 or 6 membered heterocycle containing 0 to 2 double bonds, and 3 heteroatoms selected from the group consisting of O, N, and S, which are substituted at any position on the five or six membered heterocycle, the heterocycle being optionally unsubstituted or substituted with 1 to 3 groups of $R^a$; $X^1$ and $X^2$ are independently selected from a group consisting of: H, OH, C$_{1-15}$ alkyl, C$_{2-15}$ alkenyl, C$_{2-15}$ alkynyl, halo, OR$^3$, ORCF$_3$, C$_{5-10}$ aryl, C$_{5-10}$ aralkyl, C$_{5-10}$ heteroaryl and C$_{1-10}$ acyl, said alkyl, alkenyl, alkynyl, aryl and heteroaryl optionally substituted with 1 to 3 groups of $R^a$; $R^a$ represents a member selected from the group consisting of: halo, acyl, aryl, heteroaryl, CF$_3$, OCF$_3$, —O—, CN, NO$_2$, R$^3$, OR$^3$; SR$^3$, =N(OR), S(O)R$^3$, SO$_2$R$^3$, NR$^3$R$^3$, NR$^3$ COR$^3$, NR$^3$ CO$_2$ R$^3$, NR$^3$CON(R$^3$)$_2$, NR$^3$ SO$_2$ R$^3$, COR$^3$, CO$_2$R$^3$, CON(R$^3$)$_2$, SO$_2$ N(R$^3$)$_2$, OCON(R$^3$)$_2$ said aryl and heteroaryl optionally substituted with 1 to 3 groups of halo or C$_{1-6}$ alkyl; Y is selected from the group consisting of: S(O)$_p$, —CH$_2$—, —C(O)—, —C(O)NH—, —NR—, —O—, —SO$_2$NH—, —NHSO$_2$; $Y^1$ is selected from the group consisting of: O and C; Z is selected from the group consisting of: CO$_2$R$^3$, R$^3$CO$_2$R$^3$, CONHSO$_2$Me, CONHSO$_2$, CONH$_2$ and 5-(1H-tetrazole); t and v are independently 0 or 1 such that t+v=1 Q is a saturated or unsaturated straight chain hydrocarbon containing 2–4 carbon atoms and p is 0–2 with the proviso when Z is CO$_2$ R$^3$ and B is a 5 membered heterocycle consisting of O, R$^3$ does not represent methyl.

Additional analogs suitable for practicing the inventive methods and compositions include compounds taught in U.S. Pat. Nos. 5,847,008, 6,090,836 and 6,090,839, each of which is herein incorporated by reference in its entirety to the extent not inconsistent with the present disclosure.

Additionally a variety of suitable analogs are taught in U.S. Pat. No. 6,274,608. Aryl and heteroaryl acetic acid and oxyacetic acid analogs are taught for instance in U.S. Pat. No. 6,160,000; substituted 5-aryl-2,4-thiazolidinedione analogs are taught in U.S. Pat. No. 6,200,998; other possible analogs such as polyunsaturated fatty acids and eicosanoids are known (see for instance, Forman, B M, Chen, J, and Evans R M, PNAS 94:4312–4317. The compounds of these publications, which are each herein incorporated by reference in their entirety to the extent not inconsistent with the present disclosure can be screened by the methods provide below to provide compounds which are useful, for instance, in reducing body fat. and body weight, modulating fat catabolism, and reducing appetite according to the present disclosure.

Synthesis of Fatty Acid Alkanolamides

Compounds useful in practicing the present invention are readily synthesized and purified using methods recognized in the art. In an exemplary synthetic scheme (Scheme 1), a carboxylic acid and an aminoalcohol (or an O-protected derivative thereof) are reacted in a the presence of a dehydrating agent, e.g., dicyclohexylcarbodiimide, in an appropriate solvent. The fatty acid alkanol amide is isolated by methods such as extraction, crystallization, precipitation, chromatography and the like. If the final product is the O-protected adduct, it is deprotected, typically by an art-recognized method, to afford a fatty acid adduct having a free hydroxyl group.

Scheme 1

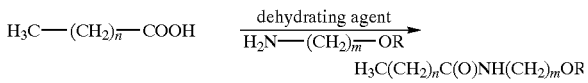

Those of skill in the art will recognize that many variants on the scheme set forth above are available. For example, an activated derivative, e.g, acyl halide, active ester, of the acid can be used. Similarly, a glycol (preferably mono O-protected) can be substituted for the amino alcohol, resulting in an ester linkage between the two constituents of the molecule.

Reverse esters and reverse amides are also readily synthesized by art-recognized methods. For example, a hydroxycarboxylic acid is reacted with an amine or hydroxy derivative of a long chain alkyl (i.e., $C_4$–$C_{22}$) in the presence of a dehydrating agent. In certain reaction pathways, it is desirable to protect the hydroxyl moiety of the hydroxycarboxylic acid.

Ethers and mercaptans are prepared by methods well-known to those of skill in the art, e.g., Williamson synthesis. For example, a long chain alkyl alcohol or thiol is deprotonated by a base, e.g, NaH, and a reactive alcohol derivative, e.g., a halo, tosyl, mesyl alcohol, or a protected derivative thereof is reacted with the resulting anion to form the ester or mercaptan.

The above-recited methods and variations thereof can be found in, for example, RECENT DEVELOPMENTS IN THE Synthesis OF FATTY ACID DERIVATIVES, Knothe G, ed., Amer. Oil Chemists Society 1999; COMPREHENSIVE NATURAL PRODUCTS CHEMISTRY AND OTHER SECONDARY METABOLITES INCLUDING FATTY ACIDS AND THEIR DERIVATIVES, Nakanishi K, ed., Pergamon Press, 1999; ORGANIC SYNTHESIS COLLECTED VOLUMES I-V, John Wiley and Sons; COMPENDIUM OF ORGANIC SYNTHETIC METHODS, Volumes 1–6, Wiley Interscience 1984; ORGANIC FUNCTIONAL GROUP PREPARATION, Volumes I-III, Academic Press Ltd. 1983; Greene T, PROTECTING GROUPS IN ORGANIC SYNTHESIS, 2d ed., Wiley Interscience 1991.

Methods of Use, Pharmaceutical Compositions, and their Administration

Methods of Use

The compounds, compositions and methods of the invention (e.g., fatty acid alkanolamides, fatty acid ethanolamide compounds, analogs, and homologues) are used to reduce body fat and or body weight in mammals, including dogs, cats, and especially humans. The weight loss may be for aesthetic or therapeutic purposes. The compounds may also be used to reduce appetite or induce hypophagia.

The compounds, compositions, and methods of the invention are used to prevent weight gain or body fat increases in individuals within a normal weight range. The compounds may be used in otherwise healthy individuals who are not otherwise in need of any pharmaceutical intervention for diseases related to diabetes or hyperlipidemia or cancer. In some embodiments, the individuals to be treated are free of diseases related to disturbances in sugar or lipid levels or metabolism or free of risk factors for cardiovascular and cerebrovascular disease. The individuals may be non-diabetic and have blood sugar levels in the normal range. The individuals may also have blood lipids (e.g., cholesterol) or triglyceride levels in the normal range. The individuals may be free of atherosclerosis. The individuals may be free of other conditions such as cancer or other tumors, disorders involving insulin resistance, Syndrome X, and pancreatitis.

In other embodiments, the subjects are overweight or obese persons in need of body fat and/or body weight reduction. In these embodiments, the methods, compounds, and compositions of the invention can be administered to promote weight loss and also to prevent weight gain once a body weight within the normal range for a person of that sex and age and height has been achieved. The compounds may be used in otherwise healthy individuals who are not in need of any pharmaceutical treatment of a disorder related to diabetes, hyperlipidemia, or cancer. The individuals may also otherwise free of risk factors for cardiovascular and cerebrovascular diseases. In some embodiments, the individuals to be treated are free of diseases related to sugar (e.g., glucose) or lipid metabolism. The individuals may be non-diabetic and have blood sugar levels in the normal range. The individuals may also have blood lipids (e.g., cholesterol, HDL, LDL, total cholesterol) or triglyceride levels in the normal range. The individuals may not need to be in treatment for atherosclerosis.

The compounds methods, and compositions of the invention may also be administered to suppress appetite in mammals, including cats, dogs, and humans. In some embodiments, the compounds may be used in otherwise healthy individuals who are not in need of pharmaceutical interventions for any disease. In some embodiments, the individuals do not need preventive or ameliorative therapy for diseases, including cancer, diabetes, or hyperlipidemia. In some embodiments, the individuals to be treated are free of diseases related to abnormal sugar or lipid levels. In other embodiments the individuals may be free of risk factors for cardiovascular or cerebrovascular disease. The individuals may be non-diabetic and have blood sugar levels in the normal range. The individuals may also have blood lipids (e.g., cholesterol) or triglyceride levels in the normal range. The individuals may be free of atherosclerosis.

The compounds methods, and compositions of the invention may also be administered to modulate fat metabolism (e.g., increase fat catabolism) in mammals, including cats, dogs, and humans. In some embodiments, the compounds may be used to reduce appetite in otherwise healthy individuals. In some embodiments, the individuals to be treated are free of diseases related to sugar or lipid metabolism (e.g., diabetes, hypercholesterolemia, low HDL levels or high LDL levels). The individuals may be non-diabetic and have blood sugar levels in the normal range. The individuals may also have blood lipids (e.g., cholesterol) or triglyceride levels in the normal range. The individuals may be free of atherosclerosis.

Treatment with the compounds and compositions of the invention may be for a period predetermined by the degree or amount of weight loss has been accomplished or when the individual achieves a BMI within the normal range. Treatment with the compounds and compositions of the invention may be reduced once a predetermined degree or amount of weight loss has been accomplished or when the individual achieves a BMI within the normal range The compounds and compositions of the invention may be administered solely for the purposes of reducing body fat or reducing appetite.

Pharmaceutical Compositions.

Another aspect of the present invention provides pharmaceutical compositions which comprise compounds of the invention and a pharmaceutically acceptable carrier.

The pharmaceutical compositions of the present invention comprise a compound of the instant invention as an active ingredient or a pharmaceutically acceptable salt thereof, and may also contain a pharmaceutically acceptable carrier and optionally other therapeutic ingredients.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend in part on the nature and severity of the conditions being treated and on the nature of the active ingredient. An exemplary route of administration is the oral route. The compositions may be conveniently presented in unit dosage form and prepared by any of the methods well-known in the art of pharmacy.

In practical use, the compounds of the invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations can contain at least 0.1 percent of active compound. The percentage of active compound in these compositions may, of course, be varied and may conveniently be between about 2 percent to about 60 percent of the weight of the unit. The amount of active compound in such therapeutically useful compositions is such that a therapeutically effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor. To prevent breakdown during transit through the upper portion of the GI tract, the composition may be an enteric coated formulation.

Administration

The compounds of the invention may also be administered parenterally. Solutions or suspensions of these active compounds can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

The compounds of the invention can be effective over a wide dosage range. For example, in the treatment of adult humans, dosages from about 10 to about 1000 mg, about 100 to about 500 mg or about 1 to about 100 mg may be needed. Doses of the 0.05 to about 100 mg, and more preferably from about 0.1 to about 100 mg, per day may be used. A most preferable dosage is about 0.1 mg to about 70 mg per day. In choosing a regimen for patients, it may frequently be necessary to begin with a dosage of from about 2 to about 70 mg per day and when the condition is under control to reduce the dosage as low as from about 0.1 to about 10 mg per day. For example, in the treatment of adult humans, dosages from about 0.05 to about 100 mg, preferably from about 0.1 to about 100 mg, per day may be used. The exact dosage will depend upon the mode of administration, on the therapy desired, form in which administered, the subject to be treated and the body weight of the subject to be treated, and the preference and experience of the physician or veterinarian in charge.

Generally, the compounds of the present invention can be dispensed in unit dosage form comprising preferably from about 0.1 to about 100 mg of active ingredient together with a pharmaceutically acceptable carrier per unit dosage. Usually, dosage forms suitable for oral, nasal, pulmonary or transdermal administration comprise from about 0.001 mg to about 100 mg, preferably from about 0.01 mg to about 50 mg of the compounds admixed with a pharmaceutically acceptable carrier or diluent. For storage and use, these preparations preferably contain a preservative to prevent the growth of microorganisms.

Administration of an appropriate amount the candidate compound may be by any means known in the art such as, for example, oral or rectal, parenteral, intraperitoneal, intravenous, subcutaneous, subdermal, intranasal, or intramuscular. In some embodiments, administration is transdermal. An appropriate amount or dose of the candidate compound may be determined empirically as is known in the art. An appropriate or therapeutic amount is an amount sufficient to effect a loss of body fat or a loss in body weight in the animal over time. The candidate compound can be administered as often as required to effect a loss of body fat or loss in body weight, for example, hourly, every six, eight, twelve, or eighteen hours, daily, or weekly Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastlles comprising the active ingredient in an inert base, such as gelatin and glycerin or sucrose and acacia emulsions, gels, and the like containing, in addition to the active ingredient, carriers known in the art.

Injection solutions and suspensions can be prepared from sterile powders, granules, and tablets of the kind previously described. Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

With respect to transdermal routes of administration, methods for transdermal administration of drugs are disclosed in Remington's Pharmaceutical Sciences, 17th Edition, (Gennaro et al. Eds., Mack Publishing Co., 1985). Dermal or skin patches are a preferred means for transdermal delivery of the compounds of the invention. Patches preferably provide an absorption enhancer such as DMSO to increase the absorption of the compounds. Other methods for transdermal drug delivery are disclosed in U.S. Pat. Nos. 5,962,012, 6,261,595, and 6,261,595. Each of which is incorporated by reference in its entirety.

Preferred patches include those that control the rate of drug delivery to the skin. Patches may provide a variety of dosing systems including a reservoir system or a monolithic system, respectively. The reservoir design may, for example, have four layers: the adhesive layer that directly contacts the skin, the control membrane, which controls the diffusion of drug molecules, the reservoir of drug molecules, and a water-resistant backing. Such a design delivers uniform amounts of the drug over a specified time period, the rate of delivery has to be less than the saturation limit of different types of skin.

The monolithic design, for example, typically has only three layers: the adhesive layer, a polymer matrix containing the compound, and a water-proof backing. This design brings a saturating amount of drug to the skin. Thereby, delivery is controlled by the skin. As the drug amount decreases in the patch to below the saturating level, the delivery rate falls.

Compounds of the invention may be used in combination with other compounds of the invention or with other drugs that may also be useful in dieting or the treatment, prevention, suppression or amelioration of body fat. Such other drugs may be administered, by a route and in an amount commonly used therefor, contemporaneously or sequentially with a compound of the invention. When a compound of the invention is used contemporaneously with one or more other drugs, a pharmaceutical composition in unit dosage form containing such other drugs and the compound is preferred. When used in combination with one or more other active ingredients, the compound of the present invention and the other active ingredients may be used in lower doses than when each is used singly. Accordingly, the pharmaceutical compositions of the present invention include those that contain one or more other active ingredients, in addition to the compounds disclosed above.

Identification of Compounds of the Invention

Candidate compounds, such as disclosed above, can be screened by a variety of means known in the art. Body fat reducing compounds, for instance, can be identified in vivo using animal bioassay techniques known to those of ordinary skill in the art. Test compounds and appropriate vehicle or caloric controls can be administered by any of a number of routes (e.g., the oral route, a parenteral route) to experimental subjects and the weight of the subjects can be monitored over the course of therapy. The experimental subjects are humans or test animals (e.g., rats, mice).

The effect of the compound on appetite or in inducing hypophagia or reduced food intake can be assessed, for instance, by monitoring the food consumption of the test subjects (e.g., measuring the amount eaten or not eaten by a subject in terms of food weight or caloric content). The effect of the compounds on appetite can also be assessed by subjective means including questionnaires as to appetite or food cravings levels by human subjects. The effect of the test compounds on lipid metabolism can be assessed by monitoring blood lipids and fatty acid oxidation. The techniques for these assessments are well known to those of ordinary skill in the art. The studies may be acute, subacute, chronic, or subchronic with respect to the duration of administration and or follow-up of the effects of the administration.

Body fat reduction can be determined, for instance, by directly measuring changes in body fat of the animal or by measuring changes in the body weight of the animal. The animal may selected from the group consisting of a mouse, a rat, a guinea pig, or a rabbit. The animal may also be an ob/ob mouse, a db/db mouse, or a Zucker rat or other animal model for a weight-associated disease. Clinical studies in humans may also be conducted.

Combinatorial Chemical Libraries

Recently, attention has focused on the use of combinatorial chemical libraries to assist in the generation of new chemical compound leads. A combinatorial chemical library is a collection of diverse chemical compounds generated by either chemical synthesis or biological synthesis by combining a number of chemical "building blocks" such as reagents. For example, a linear combinatorial chemical library such as a polypeptide library is formed by combining a set of chemical building blocks called amino acids in every possible way for a given compound length (i.e., the number of amino acids in a polypeptide compound). Millions of chemical compounds can be synthesized through such combinatorial mixing of chemical building blocks. For example, one commentator has observed that the systematic, combinatorial mixing of 100 interchangeable chemical building blocks results in the theoretical synthesis of 100 million tetrameric compounds or 10 billion pentameric compounds (Gallop et al. *J. Med. Chem.* 37(9):1233(1994)).

Preparation and screening of combinatorial chemical libraries are well known to those of skill in the art. Such combinatorial chemical libraries include, but are not limited to, p benzodiazepines (U.S. Pat. No. 5,288,514), diversomers such as hydantoins, benzodiazepines and dipeptides (Hobbs et al. *PNAS USA* 90: 6909(1993)), analogous organic syntheses of small compound libraries (Chen et al.) *J. Amer. Chem. Soc.* 116: 2661(1994), oligocarbamates (Cho, et al., *Science* 261: 1303(1993)), and/or peptidyl phosphonates (Campbell et al., *J. Org. Chem.* 59: 658 (1994)), and small organic molecule libraries (see, e.g., benzodiazepines (Baum *C&EN*, January 18, page 33(1993)), thiazolidinones and metathiazanones (U.S. Pat. No. 5,549, 974), pyrrolidines (U.S. Pat. Nos. 5,525,735 and 5,519,134), benzodiazepines (U.S. Pat. No. 5,288,514), and the like.

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.).

A number of well known robotic systems have also been developed for solution phase chemistries. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, HewlettPackard, Palo Alto, Calif.) which mimic the manual synthetic operations performed by a chemist. Any of the above devices are suitable for use with the present invention. The nature and implementation of modifications to these devices so that they can operate as discussed herein will be apparent to persons skilled in the relevant art. In addition, numerous combinatorial libraries are themselves commercially available (see, e.g., ComGenex, Princeton, N.J., Asinex, Moscow, Ru, Tripos, Inc., St. Louis, Mo., ChemStar, Ltd., Moscow, RU, 3D Pharmaceuticals, Exton, Pa., Martek Biosciences, Columbia, Md., etc.).

High Throughput Assays of Chemical Libraries

The assays for compounds described herein are amenable to high throughput screening. Preferred assays thus detect activation of transcription (i.e., activation of mRNA production) by the test compound(s), activation of protein expression by the test compound(s), or binding to the gene product (e.g., expressed protein) by the test compound(s); or effects on fatty acid modulation as described below.

High throughput assays for the presence, absence, or quantification of particular protein products or binding assays are well known to those of skill in the art. Thus, for example, U.S. Pat. No. 5,559,410 discloses high throughput screening methods for proteins, and U.S. Pat. Nos. 5,576,220 and 5,541,061 disclose high throughput methods of screening for ligand/antibody binding.

In addition, high throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols the various high throughput. Thus, for example, Zymark Corp. provides technical bulletins describing screening systems for detecting the modulation of gene transcription, ligand binding, and the like.

Determining Whether Compounds Affect Food Intake, Body Weight, Body Fat, Appetite, Food Seeking Behavior, or Modulate Fatty Acid Oxidation Compounds of the invention can be administered to an animal to determine whether they affect food intake and body weight, body fat, appetite, food seeking behavior, or modulate modulator fatty acid oxidation.

Animals can be, for example, obese or normal guinea pigs, rats, mice, or rabbits. Suitable rats include, for example, Zucker rats. Suitable mice include, for example, normal mice, ALS/LtJ, C3.SW-H-$2^b$/SnJ, (NON/LtJxNZO/HlJ)F1, NZO/HlJ, ALR/LtJ, NON/LtJ, KK.Cg-AALR/LtJ, NON/LtJ, KK.Cg-A$^y$/J, B6.HRS(BKS)-Cpe$^{fat}$/+, B6.129P2-Gck$^{tm1Efr}$, B6.V-Lep$^{ob}$, BKS.Cg-m+/+Lep$^{rd}$b, and C57BL/6J with Diet Induced Obesity.

Administration of an appropriate amount the candidate compound may be by any means known in the art such as, for example, oral or rectal, parenteral such as, for example, intraperitoneal, intravenous, subcutaneous, subdermal, intranasal, or intramuscular. Preferably administration may be intraperitoneal or oral. An appropriate effective amount of the candidate compound may be determined empirically as is known in the art. An appropriate effective amount may be an amount sufficient to effect a loss of body fat or a loss in body weight or reduction in food consumption in the animal over time. The candidate compound can be administered as often as required to effect a loss of body fat or loss in body weight, for example, hourly, every six, eight, twelve, or eighteen hours, daily, or weekly.

Formulations suitable for oral administration include (a) liquid solutions, such as an effective amount of the candidate compound suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

Injection solutions and suspensions can be prepared from sterile powders, granules, and tablets of the kind previously described. Formulations suitable for parenteral administration, include, for example, aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The dose administered to the animal is sufficient to effect a change in body weight, body fat, and/or fatty acid oxidation over time. Such a dose can be determined according to the efficacy of the particular candidate compound employed and the condition of the animal, as well as the body weight or surface area of the animal. The size of the dose also will be determined by the existence, nature, and extent of any adverse side-effects that accompany the administration of a candidate compound; the $LD_{50}$ of the candidate compound; and the side-effects of the candidate compound at various concentrations. In general, the dose will range from 0.1–50 mg per kg, preferably 1–25 mg per kg, most preferably 1–20 mg per kg body weight. The determination of dose response relationships is well known to one of ordinary skill in the art.

Body Fat Reduction

Body weight reduction is typically determined by direct measurements of the change in body fat or by loss of body weight. Body fat and body weight of the animals is determined before, during, and after the administration of the candidate compound. Changes in body fat are measured by any means known in the art such as, for example, fat fold measurements with calipers, bioelectrical impedance, hydrostatic weighing, or dual x-ray absorbiometry. Preferably animals demonstrate at least 2%, 5%, 8%, or 10% loss of body fat. Changes in body weight can be measured by any means known in the art such as, for example, on a portable scale, on a digital scale, on a balance scale, on a floor scale, or a table scale. Preferably animals demonstrate at least 2%, 5%, 10%, or 15% loss of body weight. Body weight reduction is measured before administration of the candidate compound and at regular intervals during and after treatment. Preferably, body weight is measured every 5 days, more preferably every 4 days, even more preferably every 3 days, yet more preferably every 2 days, most preferably every day.

Changes in Fatty Acid Metabolism

Changes in fatty acid metabolism can be measured, for instance, by looking at fatty acid oxidation in cells from major fat burning tissues such as, for example, liver (Beynen, et al. *Diabetes* 28:828 (1979)), muscle (Chiasson Lab. Anat. of Rat, (1980)), heart (Flink, et al. *J. Biol. Chem.* 267: 9917 (1992)), and adipocytes (Rodbell *J. Biol. Chem.* 239: 375 (1964)), Cells may be from primary cultures or from cell lines. Cells may be prepared for primary cultures by any means known in the art including, for example, enzymatic digestion and dissection. Suitable cell lines are known to those in the art. Suitable hepatocyte lines are, for example, Fao, MH1C1, H-4-II-E, H4TG, H4-II-E-C3, McA-RH7777, McA-RH8994, N1-S1 Fudr, N1-S1, ARL-6, Hepa 1–6, Hepa-1c1c7, BpRcl, tao BpRcl, NCTC clone 1469, PLC/PRF/5, Hep 3B2.1–7 [Hep 3B], Hep G2 [HepG2], SK-HEP-1, WCH-17. Suitable skeletal muscle cell lines are, for example, L6, L8, C8, NOR-10, BLO-11, BC3H1, G-7, G-8, C2C12, P19, So18, SJRH30 [RMS 13], QM7. Suitable cardiac cell lines are, for example, H9c2(2-1), P19, CCD-32Lu, CCD-32Sk, Girardi, FBHE. Suitable adipocyte lines are, for example, NCTC clone 929 [derivative of Strain L; L-929; L cell], NCTC 2071, L-M, L-M (TK-) [LMTK-; LM(tk-)], A9 (APRT and HPRT negative derivative of Strain L), NCTC clone 2472, NCTC clone 2555, 3T3-L1, J26, J27-neo, J27-B7, MTKP 97-12 pMp97b [TKMp97-12], L-NGC-5HT2, LtK-11, L-alpha-1b, L-alpha-2A, L-alpha-2C, B82.

The rate of fatty acid oxidation may be measured by $^{14}C$-oleate oxidation to ketone bodies (Guzmán and Geelen Biochem. J. 287:487 (1982)) and/or $^{14}C$-oleate oxidation to $CO_2$ (Fruebis PNAS 98:2005 (2001); Blazquez et al. *J. Neurochem* 71: 1597 (1998)). Lypolysis may be measured by fatty acid or glycerol release by using appropriate labeled precursors or spectrophotometric assays (Serradeil-Le Gal *FEBS Lett* 475: 150 (2000)). For analysis of $^{14}C$-oleate oxidation to ketone bodies, freshly isolated cells or cultured cell lines can be incubated with $^{14}C$-oleic acid for an appropriate time, such as, for example, 30, 60, 90, 120, or 180 minutes. The amount of $^{14}C$ radioactivity in the incubation medium can be measured to determine their rate of oleate oxidation. Oleate oxidation can be expressed as nmol oleate produced in x minutes per g cells. For analysis of lypolysis/glycerol release, freshly isolated cells or cultured cells lines can be washed then incubated for an appropriate time. The amount of glycerol released into the incubation media can provide an index for lypolysis.

EXAMPLES

The following examples are provided by way of illustration only and not by way of limitation. Those of skill will readily recognize a variety of non-critical parameters which could be changed or modified to yield essentially similar results.

Example 1

Synthesis of Fatty Acid Ethanolamide Compounds, Homologues and Analogs

Methods for the formation of fatty acid ethanolamines from ethanolamines and the corresponding fatty acyl are relatively straight forward and known to one of ordinary skill in the art. For example, fatty acid ethanolamides may be synthesized by reacting a fatty acid or fatty acid chloride with an aminoalcohol as described by Abadjj et al. (Abadji, V., Lin, S. Y., Taha, G., Griffin, G., Stevenson, L. A., Pertwee, R. G. & Makriyannis, A. *J. Med. Chem.* 37, 1889–1893 (1994)). Fatty acids may be prepared similarly to the procedure of Serdarevich and Carroll (Serdarevich, B. & Carroll, K. K. *J. Lipid Res.* 7, 277–284 (1966)). Radioactively labeled fatty acid ethanolamides can be prepared by reaction with acyl chlorides (Nu-Check Prep, Elysian, Minn.) with [$^3$H]ethanolamine (10–30 Ci/mmol; American Radiolabeled Chemicals, St. Louis) as described by Desarnaud, F., Cadas, H. & Piomelli, D. (1995) *J. Biol. Chem.* 270, 6030–6035. Compounds can be purified by flash column chromatography or HPLC. Compound identity can be established by use of NMR and/or gas chromatography-mass spectrometry and thin layer chromatography.

Starting reagents and materials may be purchased from Avanti Polar Lipids, Cayman Chemicals (Ann Arbor, Mich.), Nu-Check Prep, Research Biochemicals, or Sigma. Briefly, according to methods taught by Giuffrida, A. et al. (see Giuffrida, A and Piomelli, D. in Lipid Second Messengers (Laycock, S. G. and Rubin, R. P. Eds. pp. 113–133 CRC Press LLC, Boca Raton, Fla.) and Devane et al. (Devane W., Hanus, L. et al. *Science* 258, 1946–1949 (1992)), unlabeled or labeled fatty acyl ethanolamines can be synthesized by the reaction of the corresponding fatty acyl chlorides with unlabeled or labeled ethanolamine. The fatty acid chorides can be dissolved in dichloromethane (10 mg/ml) and reacted with ethanolamine at –0.4° C. for 15 minutes. The reaction can be quench by the addition of purified water. After vigorous stirring the phases are allowed to separate. The upper aqueous phase is discarded. The organic phase is washed twice with water. These washes remove the unreacted ethanolamine. This method provides a quantitative formation of fatty acyl ethanolamines. The ethanolamines are concentrated to dryness under a stream of nitrogen gas and can be reconstituted in an organic solvent such as dichloromethane at a concentration of 20 mM. The resulting fatty acyl ethanolamine solution can be stored at –20° C. until needed for use.

The chemistry of fatty acid carboxylic acid groups, primary and secondary amines, and primary alcohol groups is well known to one of ordinary skill in the art. Fatty acid ethanolamides having a variety of substituents on the ethanolamine portion thereof can be formed in many ways, but most preferably by starting with the corresponding substituted ethanolamine and fatty acid moieties. Such substituted ethanolamines would include the alkyl aminoethanol ethers and acyl aminoethanol esters as well as secondary akyl ethanol amines. Alternatively, the particular fatty acid ethanolamide can be synthesized from the corresponding fatty acid ethanolamide by the addition of the appropriate substituent groups.

Example 2

Methods for Screening Fatty Acid Ethanolamide (FAE) in vivo and Other Compounds of the Invention.

Animals. Male Wistar rats (200–350 g) were used. Procedures should met NIH guidelines detailed in the Guide for the Care and Use of Laboratory Animals, and the European Communities directive 86/609/EEC regulating animal research.

Chemicals. FAEs and [$^2H_4$] FAEs were synthesized in the laboratory (Giuffrida et al., "*Lipid Second Messengers*" (ed. Laychock, S. G. & Rubin, R. P.) 113–133 (CRC Press LLC, Boca Raton, Fla., 1998)); 1,2-dioleyl-sn-glycero-phosphoethanolamine-N-oleyl was purchased from Avanti Polar Lipids (Alabaster, Ala.); SR141716A was provided by RBI (Natick, Mass.) as part of the Chemical Synthesis Program of the NIMH (N01MH30003); SR144528 was a generous gift of Sanofi Recherche; all other drugs were from Tocris (Ballwin, Mo.) or Sigma (Saint Louis, Mo.). FAE were dissolved in dimethylsulphoxide (DMSO) and administered in 70% DMSO in sterile saline (acute treatments) or 5% Tween 80/5% propylenglycol in sterile saline (subchronic treatments) (1 ml per kg, i.p.). Capsaicin was administered in 10% Tween 80/10% ethanol/80% saline; SR141716A, SR144528, CCK-8 and CP-93129 in 5% Tween 80/5% propylenglycol/90% saline (1 ml per kg, i.p.).

Enzyme assays. In all biochemical experiments, rats were killed and tissues collected between 1400 and 1600 h, after varying periods of food deprivation. Microsome fractions were prepared as described (Désarnaud et al., *J. Biol. Chem.*, 270:6030–6035 (1995)). NAT assays were performed using 1,2-di[$^{14}$C]palmityl-sn-glycerophosphocholine as a substrate (108 mCi/mmol, Amersham, Piscataway, N.J.) (Cadas et al., H., *J. Neurosci.*, 17:1226–1242 (1997)). FAAH assays were performed according to (Désarnaud et al., *J. Biol. Chem.*, 270:6030–6035 (1995)), except that [$^3$H] anandamide (arachidonyl-[1-$^3$H]ethanolamide; 60 Ci/mmol; ARC, St. Louis, Mo.) was included as a substrate and radioactivity was measured in the aqueous phase after chloroform extraction.

HPLC/MS analyses. Plasma was prepared from blood obtained by cardiac puncture (Giuffrida et al., *Anal. Biochem.*, 280:87–93 (2000)) and CSF was collected from the cisterna magna using a 27G ½ needle (Precisionglide, USA). FAEs and NAPE were extracted from tissues with methanol/chloroform and fractionated by column chromatography (Giuffrida et al., "Lipid Second Messengers" (ed. Laychock, S. G. & Rubin, R. P.) 113–133 (CRC Press LLC, Boca Raton, Fla., 1998)). FAEs were quantified by HPLC/MS, using an isotope dilution method (Giuffrida et al., *Anal. Biochem.*, 280:87–93 (2000)). Individual NAPE species were identified and quantified by HPLC/MS, using an external standard method (Calignano et al., *Nature*, 408:96–101 (2000)).

Blood chemistry. Plasma β-hydroxybutyrate and glycerol were measured using commercial kits (Sigrna, St. Louis, Mo.). Plasma prolactin, corticosterone and luteinizing hormone were quantified by radioimmunoassay (Navarro et al., *Neuroreport*, 8:491–496 (1997)).

Feeding experiments. Acute experiments. Food intake was measured in 24-h food-deprived rats (Navarro et al., *J. Neurochem.*, 67:1982–1991 (1996)), administering drugs 15 min before food presentation. Subchronic experiments. Ad libitum fed rats received vehicle injections for three days. On day four, the animals were divided in two equal groups and gave them daily injections of vehicle or OEA (5 mg per kg at 1900 h) for 7 consecutive days, while measuring body weight, food intake and water intake.

Conditioned taste aversion. Rats were water-deprived for 24 h and then accustomed to drink from a graded bottle during a 30-min test period for four days. On day five, water was substituted with a 0.1% saccharin solution and, 30 min later, the animals received injections of vehicle, OEA (20 mg per kg) or lithium chloride (0.4 M, 7.5 ml per kg). During the following two days, water consumption was recorded over 30-min test periods. The animals were then presented with water or saccharin, and drinking measured.

Operant responses for food. Rats were trained to lever press for food on a fixed ratio 1 (FR1) schedule of reinforcement, while food-restricted at 20 g of chow per rat per day (Rodriguez de Fonseca et al., *Acta Pharmacol. Sin.*, 20:1109–1114 (1999)). Once stable responding was achieved, the animals were trained to acquire an FR5, time out 2-min schedule of food reinforcement and kept in limited access to food. When a stable baseline was obtained, the animals were used to test the effects of vehicle or OEA (1, 5 or 20 mg per kg) administered 15 min before lever presentation. Test duration was 60 min.

Other behavioral assays. The elevated plus maze test was conducted as described (Navarro et al., *Neuroreport*, 8:491–496 (1997)) after the administration of vehicle or OEA (20 mg per kg, i.p.). Horizontal activity in an open field (Beltramo et al., *J. Neurosci.*, 20:3401–3407 (2000)) and pain threshold in the hot plate test (55° C.) (Beltramo et al., *Science*, 277:1094–1097 (1997)) were measured 15 min after injection of vehicle or OEA (20 mg per kg). Rectal temperature was measured using a digital thermometer (Martin-Calderón et al., *Eur. J. Pharmacol.*, 344:77–86. (1998)).

In situ hybridization. Rats were accustomed to the handling and injection procedure for five days. On day six, vehicle or drug OEA (10 mg per kg, i.p.), or oleic acid (10 mg per kg) was administered, and the rats killed 60 min later by decapitation under anesthesia. In situ hybridization analyses were conducted using $^{35}$S-labeled cRNA probes for c-fos (Guthrie et al., *Proc. Natl. Acad. Sci. U.S.A.*, 90:3329–3333 (1993)) and choline acetyl transferase (ChAT) (Lauterbom et al., *Brain Res. Mol. Brain Res.*, 17:59–69 (1993)). Average hybridization densities were determined from at least three tissue sections per rat. Statistical significance was evaluated using one-way analysis of variance (ANOVA) followed by the Tukey-Kramer post-hoc test for paired comparisons.

Data analysis. Results are expressed as mean±s.e.m of n separate experiments. The significance of differences among groups was evaluated using ANOVA followed by a Student-Newman-Keuls post hoc test, unless indicated otherwise.

Example 3

Effects of Starvation on OEA and Other FAE Levels in the Rat

In one embodiment, the invention provides methods of treatment wherein individuals needing to lose weight and/or body fat are tested for OEA levels before and/or during fasting. Individuals with low levels of OEA prior to or in response to fasting are particularly then targeted for OEA treatment.

Rats were deprived of food while periodically measuring FAE levels in cardiac blood by high-performance liquid chromatography (HPLC) coupled to electrospray mass spectrometry (MS). Plasma OEA remained at baseline levels for the first 12 h of fasting, markedly increased at 18–24 h, and returned to normal at 30 h (FIG. 1a). No such effect was observed following water deprivation (FIG. 1b) or application of stressors such as restraint immobilization and lipopolysaccharide (LPS) administration [in pmol per ml; 10.3±0.8; 60 min after a 15-min immobilization, 8.4±1.6; 60 min after LPS injection (1 mg per kg), 7.0±0.7; n=6–9]. Plasma PEA was not significantly affected by any of these treatments (data not shown), whereas anandamide decreased rapidly upon food removal, remaining lower than baseline for the entire duration of the experiment (FIG. 1d). Anandamide levels also declined after immobilization (in pmol per ml; control, 3.6±0.4; immobilization, 1.1±0.5; n=7–8; P<0.01), LPS treatment (control, 2.0±0.5; LPS, 0.2±0.2; n6; P<0.01) and, though not significantly, water deprivation (FIG. 1e). These results indicate that circulating OEA levels increase transiently during starvation. This response is selective for OEA over anandamide and other FAEs, and coincides temporally with the rise in blood glycerol and β-hydroxybutyrate (Table 1), which signals the shift of energy metabolism from carbohydrates to fatty acids as primary fuel (Cahill, G. F., *Clin. Endocrinol. Metab.*, 5:397–415 (1976)).

TABLE 1

Plasma level of β-hydroxybutyrate (β-HBA) and glycerol in fasting rats.

|  | β-HBA | Glycerol |
|---|---|---|
| Free feeding | 1.2 ± 0.4 | 4.6 ± 0.9 |
| 2 h fasted | 1.2 ± 0.2 | 5.3 ± 0.6 |
| 4 h fasted | 0.8 ± 0.1 | 9.1 ± 1.8 |
| 8 h fasted | 1.3 ± 0.2 | 6.3 ± 0.4 |
| 12 h fasted | 4.6 ± 0.8* | 7.6 ± 1.0 |
| 18 h fasted | 6.8 ± 0.4* | 8.4 ± 0.4* |
| 24 h fasted | 9.1 ± 1.2* | 8.4 ± 0.3* |

Concentrations are expressed in mg per dl. *$P < 0.05$, n = 3 per group.

Figure 2:
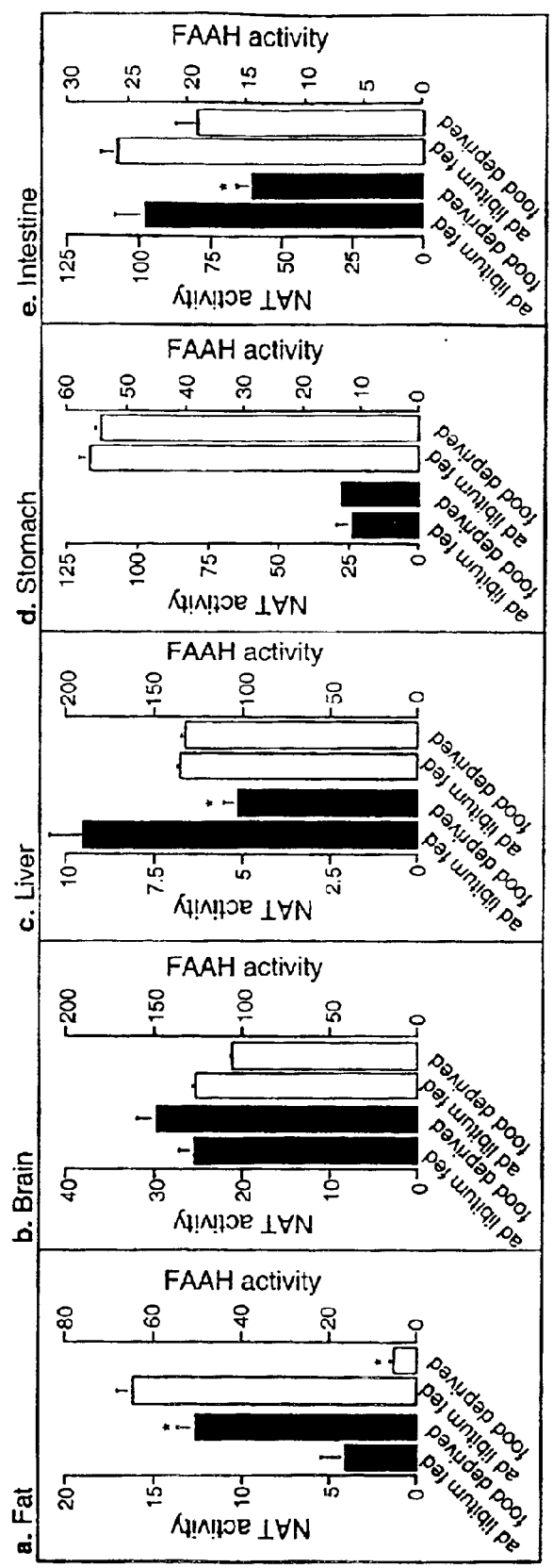
FIG. 2. Adipose tissue is a primary source of circulating oleoylethanolamide: starvation-induced changes in N-acyltransferase (NAT) and fatty acid amide hydrolase (FAAH) activities in various rat tissues. (a) fat; (b) brain; (c) liver; (d) stomach; (e) small intestine. Empty bars, free-feeding animals; filled bars, 18-h fasted animals. Activities are in pmol/mg protein/min. Asterisk, $P<0.05$, $n=3$.
Figure 3:
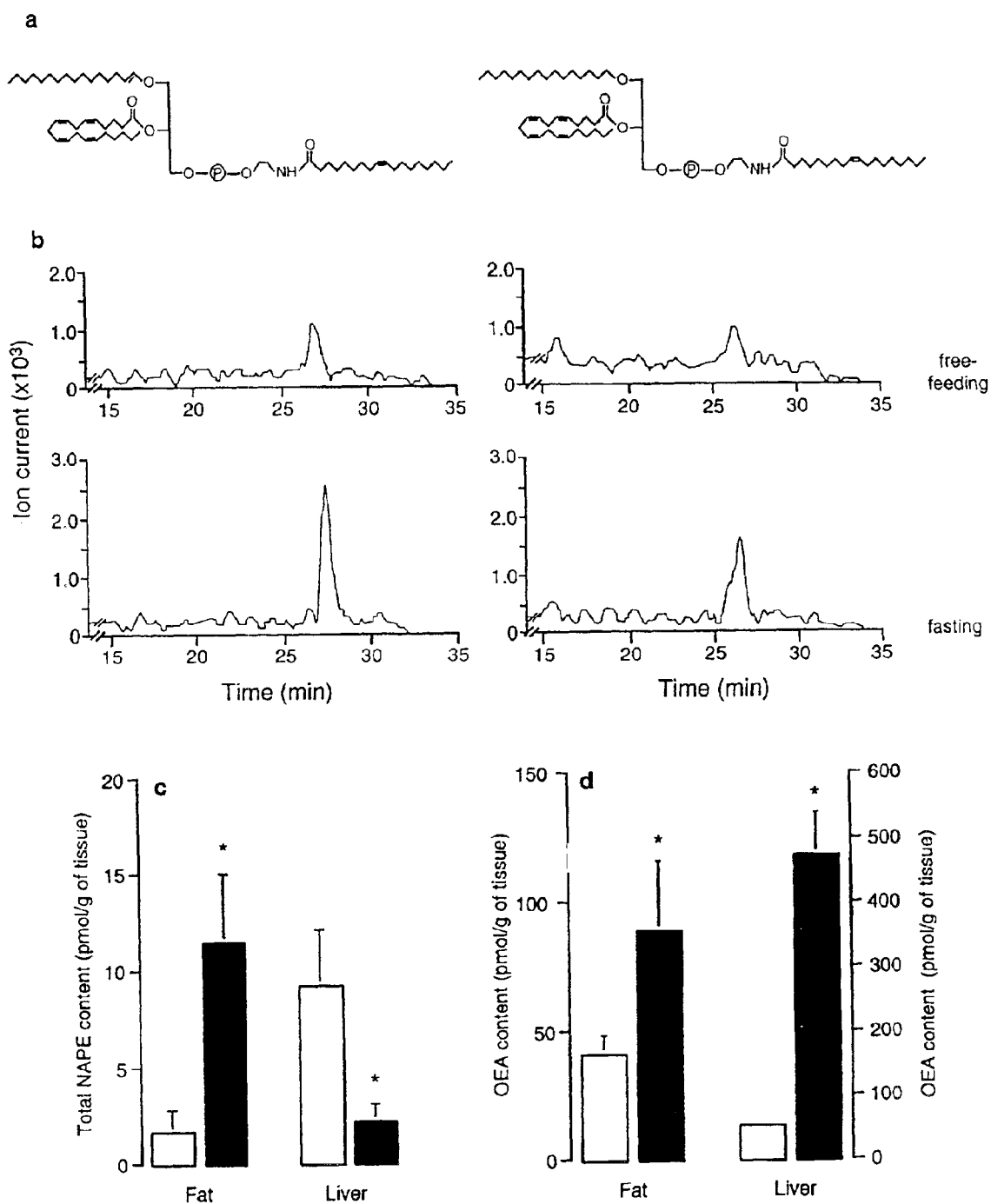
FIG. 3. Adipose tissue is a primary source of circulating oleoylethanolamide: starvation-induced changes in NAPE and oleoylethanolamide (oleoylethanolamide, OEA) content in adipose and liver tissues. (a) structures of the oleoylethanolamide precursors alk-1-palmitoenyl-2-arachidonyl-snglycero-phosphoethanolamine-N-oleyl (left panel, NAPE 1) and alk-1-palmityl-2-arachidonyl-sn-glycero-phosphoethanolamine-N-oleyl (right panel, NAPE 2); (b) representative HPLC/MS tracings for selected ions characteristic of NAPE 1 (left panel, m/z=987, deprotonated molecule, [M–H]⁻) and NAPE 2 (right panel, m/z=1003, [M–H]⁻) in free-feeding (top) and 18-h fasting rats (bottom); (c) food deprivation (18 h) increases the content of NAPE species in fat and decreases it in liver. All identifiable NAPE species were quantified, including the oleoylethanolamide precursors NAPE1 and NAPE 2, and the PEA precursor NAPE 3; (d) food deprivation (18 h) increases oleoylethanolamide content in fat and liver. Empty bars, free-feeding animals; filled bars, 18-h fasted animals. Asterisk, $P<0.05$, Student's t test; n=3.

OEA levels in cerebrospinal fluid were not significantly affected by food deprivation (FIG. 1c), implying that the surge in plasma OEA may originate outside the CNS. To test this hypothesis, the impact of starvation on OEA metabolism in various rat tissues was investigated. The biochemical route by which animal cells produce and degrade OEA and other FAEs is thought to comprise three key enzymatic steps. Calcium ion-stimulated NAT activity transfers a fatty acid group from the sn-1 position of a donor phospholipid to the primary amine of phosphatidylethanolamine, producing NAPE2 (Schmid et al., *Chem. Phys. Lipids*, 80:133–142 (1996); Piomelli et al., *Neurobiol. Dis.*, 5:462–473 (1998)). Cleavage of the distal phosphodiester bond in NAPE by an unknown phospholipase D generates FAEs (Schmid et al., *Chem. Phys. Lipids*, 80:133–142 (1996); Piomelli et al., *Neurobiol. Dis.*, 5:462–473 (1998)), which are eventually broken down to fatty acid and ethanolamine by an intracellular fatty acid amide hydrolase (FAAH) (Schmid et al., *J. Biol. Chem.*, 260:14145–14149 (1985); Cravatt et al., *Nature*, 384:83–87 (1996)). Food deprivation (18 h) was accompanied by a marked increase in NAT activity in white adipose tissue (FIG. 2a), but not in the brain, stomach or kidney (FIGS. 2b,d and data not shown). In liver, intestines and skeletal muscle, NAT activity was reduced by fast (FIGS. 2c,d and data not shown). These enzymatic changes were paralleled by corresponding alterations in NAPE tissue content. Several molecular species of NAPE are present in rat tissues, including the OEA precursors alk-1-palmitoenyl-2-arachidonyl-sn-glycero-phosphoethanolamine-N-oleyl (NAPE 1; FIG. 3a) and alk-1-palmityl-2-arachidonyl-sn-glycero-phosphoethanolamine-N-oleyl (NAPE 2; FIG. 3a); and the PEA precursor alk-1-palmityl-2-arachidonyl-sn-glycero-phosphoethanolamine-N-palmityl (not shown). In agreement with NAT activity measurements, food deprivation increased NAPE content in fat, and decreased it in liver (FIGS. 3b,c).

Since NAPE biosynthesis and FAE formation are tightly coupled processes (Cadas et al., H., *J. Neurosci.*, 17:1226–1242 (1997)), one might expect starvation to augment the levels of OEA and other FAEs in adipose, but not in other tissues. Accordingly, fat from starved rats contained more OEA and PEA than did fat from free-feeding controls (FIG. 3d and data not shown), whereas no such difference was seen in the brain, stomach, and intestines (data not shown). Contrary to our expectation, however, the liver content of OEA and PEA was also higher in food-deprived than in free-feeding rats (FIG. 3d and data not shown). This discordance may be due to an accumulation of FAEs by the liver, which is consistent with the postulated roles of this organ in FAE recapture and metabolism (Bachur et al., *J. Biol. Chem.*, 240:1019–1024 (1965); Schmid et al., *J. Biol. Chem.*, 260:14145–14149 (1985)).

The hydrolysis to fatty acid and ethanolamine, catalyzed by FAAH, is a key step in FAE degradation (Bachur et al., *J. Biol. Chem.*, 240:1019–1024 (1965); Schmid et al., *J. Biol. Chem.*, 260:14145–14149 (1985); Cravatt et al., *Nature*, 384:83–87 (1996); Désarnaud et al., *J. Biol. Chem.*, 270:6030–6035 (1995)). Food deprivation profoundly reduced FAAH activity in adipose membranes, but had no effect on FAAH activity in the brain, liver, stomach, intestines, kidney and skeletal muscle (FIGS. 2a–e and data not shown). Thus, food deprivation may increase the levels of OEA and other FAEs in white fat in two synergistic ways, which are mechanistically distinct from other reactions occurring during lipolysis: stimulation of NAT activity may lead to increase the biosynthesis of NAPE and FAEs, while inhibition of FAAH activity may prolong the life span of newly synthesized FAEs. Although several tissues may contribute to the normal levels of OEA in the bloodstream, the dynamic biochemical changes observed in fat underscore the crucial role of this tissue in generating OEA during starvation.

Example 4

Suppression of Food Intake by OEA and Other FAEs

Figure 4:
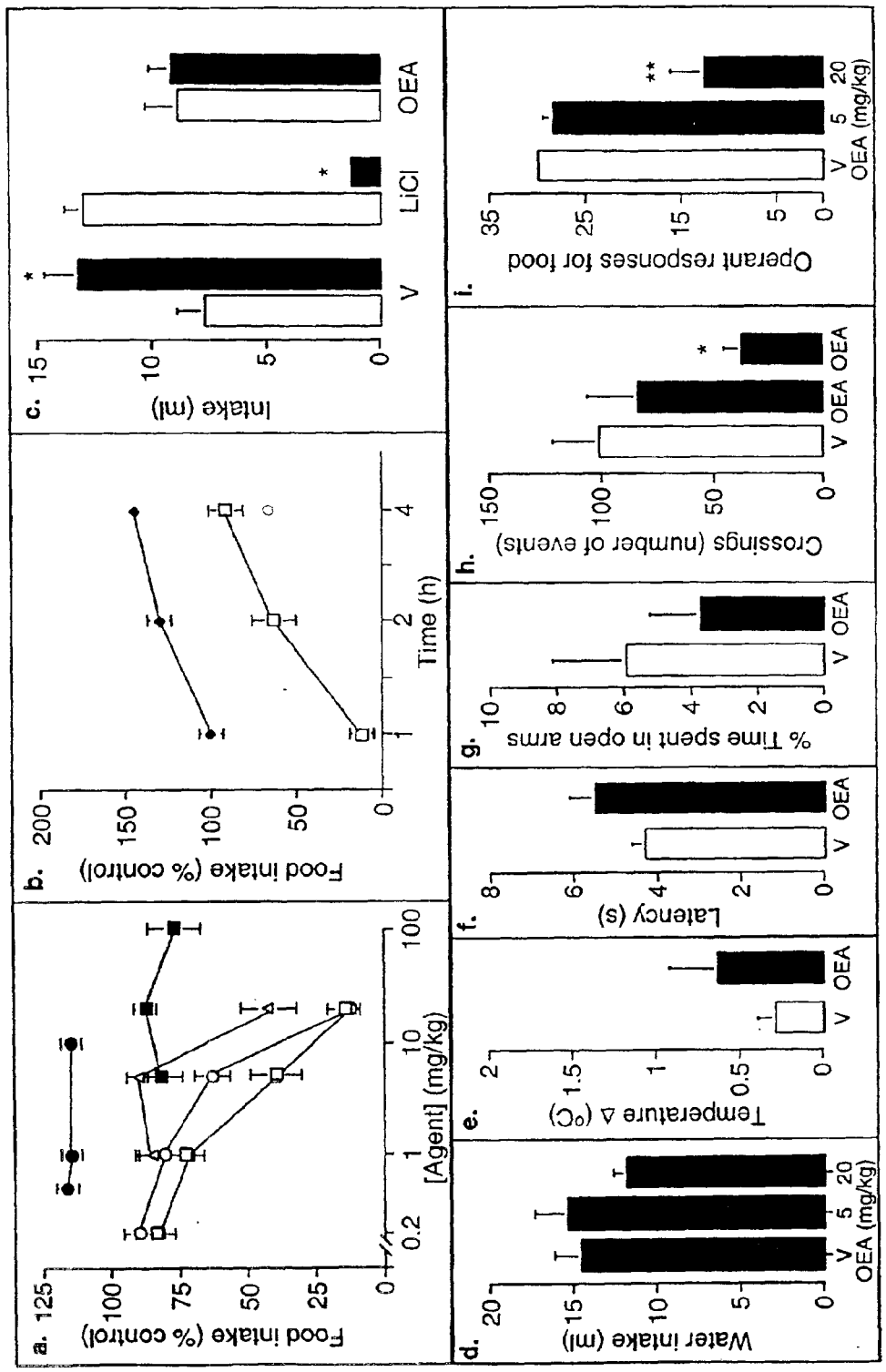
FIG. 4. Oleoylethanolamide/pranamide selectively suppresses food intake: (a) dose-dependent effects of oleoylethanolamide (oleoylethanolamide/OEA/pranamide) (i.p., empty squares), elaidylethanolamide (empty circles), PEA (triangles), oleic acid (filled squares) and anandamide (filled circles) on food intake in 24-h food-deprived rats. Vehicle alone (70% DMSO in saline, 1 ml per kg, i.p.) had no significant effect on acute food intake; (b) time course of the hypophagic effects of oleoylethanolamide (20 mg per kg, i.p.) (squares) or vehicle (lozenges) on food intake. (c) effects of vehicle (V), lithium chloride (LiCl, 0.4 M, 7.5 ml per kg) or oleoylethanolamide (20 mg per kg) in a conditioned taste aversion assay. Empty bars, water intake; filled bars, saccharin intake. Effects of vehicle (V) or oleoylethanolamide (5 or 20 mg per kg) on: (d) water intake (expressed in ml per 4 h); (e) body temperature; (f) latency to jump in the hot plate analgesia test; (g) percent time spent in open arms in the elevated plus maze anxiety test; (h) number of crossings in the open field activity test; (i) number of operant responses for food. Asterisk, $P<0.05$, n=8–12 per group.

The effects of systemically administered OEA on food intake in rats can be assessed using a 24 h fast. In this system, OEA caused a dose- and time-dependent suppression of food intake (FIGS. 4a,b). To define the selectivity of this response, various OEA analogs were evaluated for their ability to produce hypophagia.

Anandamide and oleic acid had no effect.

Palmitylethanolamide was active but significantly less potent than OEA.

Elaidylethanolamide (an unnatural OEA analog) was similar in potency to OEA (FIG. 4a).

These results indicate that OEA reduces eating in a structurally selective manner and that other fatty acid ethanolamide-like compounds can be identified for use according to the invention.

Example 5

Specificity Over Cannabinoid Receptor Activators

The molecular requisites for OEA hypophagia are distinct from those involved in the interaction of anandamide with its known cannabinoid targets (Khanolkar et al., *Life Sci.*, 65:607–616 (1999)). Cannabinoid receptor antagonists did not affect OEA hypophagia in vivo, and OEA did not displace cannabinoid binding to rat brain membranes in vitro. Thus, despite its structural and biogenetic relationships with anandamide, OEA does not depend on the endogenous cannabinoid system to produce anorexia.

Example 6

Sustained Body Weight Reduction

In some embodiments, the compounds of the instant invention provide for a sustained fat reduction or body weight reduction upon prolonged administration to mammals. This effect is advantageous as a variety of drugs suppress eating after acute administration, but fail to do so when treatment is prolonged (Blundell, J., *Trends Pharmacol. Sci.,* 12:147–157 (1991)).

Figure 5:
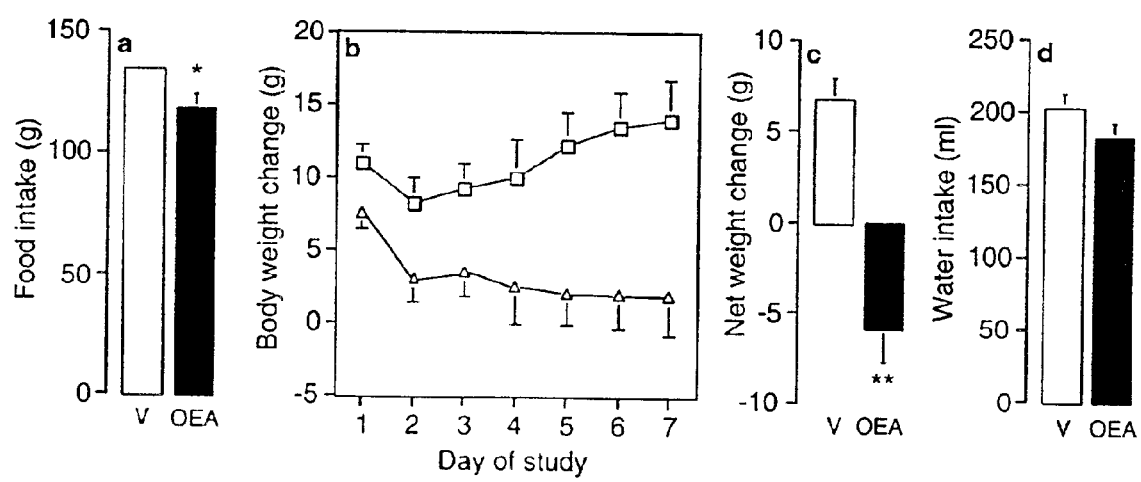
FIG. 5. Effects of subchronic oleoylethanolamide administration on food intake and body weight: (a) effects of oleoylethanolamide (oleoylethanolamide, OEA) (5 mg per kg, i.p. once a day) (empty bars) or vehicle (5% Tween 80/5% propyleneglycol in sterile saline; filled bars) on cumulative food intake; (b) time course of the effects of oleoylethanolamide (triangles) or vehicle (squares) on body weight change; (c) effects of oleoylethanolamide or vehicle on net body weight change; (d) effects of oleoylethanolamide (5 mg per kg) or vehicle on cumulative water intake. Asterisk, $P<0.05$; two asterisks, $P<0.01$, n=10 per group.

OEA was subchronically administered to rats. Daily injections of OEA (5 mg per kg, i.p.) for seven days resulted in a small, but significant decrease in cumulative food intake (FIG. 5a), which was accompanied by a profound inhibition of weight gain (FIGS. 5b,c). OEA did not affect water intake (FIG. 5d). The impact of OEA on body weight is only partially explained by its moderate reduction of food consumption indicating that other factors, such as stimulation of energy expenditure or inhibition of energy accumulation, may contribute to this effect.

Example 7

FAE's May Have a Peripheral Site of Action

In one of its aspects, the invention provides compounds with a peripheral site of action. Such a site is advantageous in reducing the likelihood of central nervous system side effects.

Figure 6:
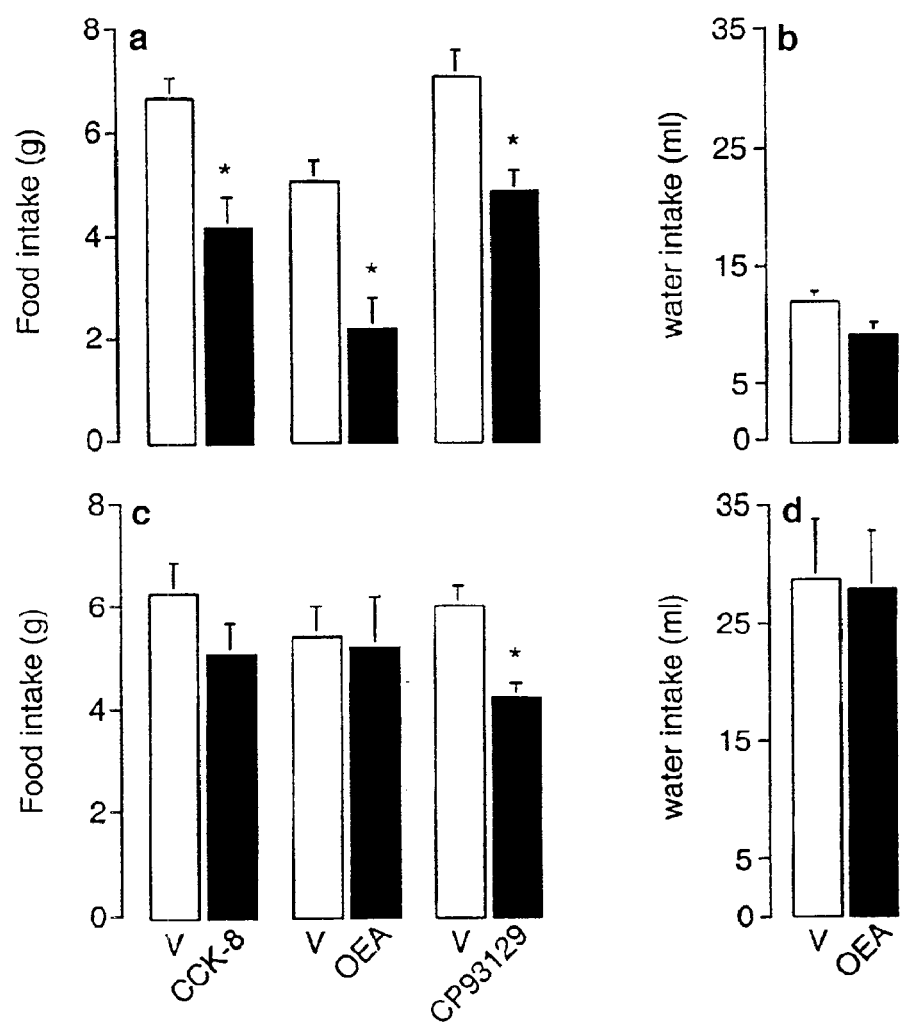
FIG. 6. Role of peripheral sensory fibers in oleoylethanolamide-induced anorexia. Effects of vehicle (V), oleoylethanolamide (oleoylethanolamide/pranamide/OEA) (5 mg per kg, i.p.), CCK-8 (10 μg per kg) and CP-93129 (1 mg per kg), a centrally active 5-HT$_{1B}$ receptor agonist, on food intake in a, control rats and c, capsaicin-treated rats. Water intake in (b) control rats and (d) capsaicin-treated rats. Asterisk, $P<0.05$; n=8–12 per group.

Though potent when administered peripherally, OEA was ineffective after direct injection into the brain ventricles (Table 2), suggesting that the primary sites of action of this compound might be located outside the CNS. As a further demonstration, sensory fibers in the vagus and other peripheral nerves were chemically destroyed by treating adult rats with the neurotoxin, capsaicin (Kaneko et al., *Am. J. Physiol.,* 275:G1056–G1062 (1998)). Capsaicin-treated rats failed to respond to peripherally administered cholecystokinin-8 (CCK-8) (FIGS. 6,a,c), drank more water than controls (FIGS. 6b,d) and lost the corneal chemosensory reflex (data not shown), three indications that the neurotoxin had destroyed sensory afferents (MacLean, D. B., *Regul. Pept.,* 11:321–333 (1985); Ritter et al., *Am. J. Physiol.,* 248:R501–R504 (1985); Curtis et al., *Am. J. Physiol.,* 272:R704–R709 (1997)). Treated animals also failed to respond to OEA (10 mg per kg, i.p.), but responded normally to the compound CP-93129, which targets 5-HT1B receptors in the CNS (FIGS. 6a,c) (Lee et al., *Psychopharmacology,* 136:304–307 (1998)). These findings support the hypothesis that OEA causes hypophagia by acting at a peripheral site, and that sensory fibers are required for this effect.

TABLE 2

Effects of intracerebroventricular pranamide on food intake.

| | 60 min | 120 min | 240 min |
|---|---|---|---|
| vehicle | 5.8 ± 0.6 | 8.0 ± 0.5 | 9.5 ± 0.5 |
| prana 0.4 µg | 4.8 ± 0.4 | 6.6 ± 0.4 | 8.4 ± 0.4 |
| prana 2 µg | 4.9 ± 0.4 | 6.6 ± 0.6 | 8.7 ± 0.5 |
| prana 10 µg | 5.9 ± 0.2 | 8.1 ± 0.4 | 9.6 ± 0.7 |

Pranamide/OEA (prana, µg per animal) or vehicle (DMSO, 5 µl) was administered to 24 h food-deprived rats 15 min before food presentation. n = 12 per group.

Figure 7:
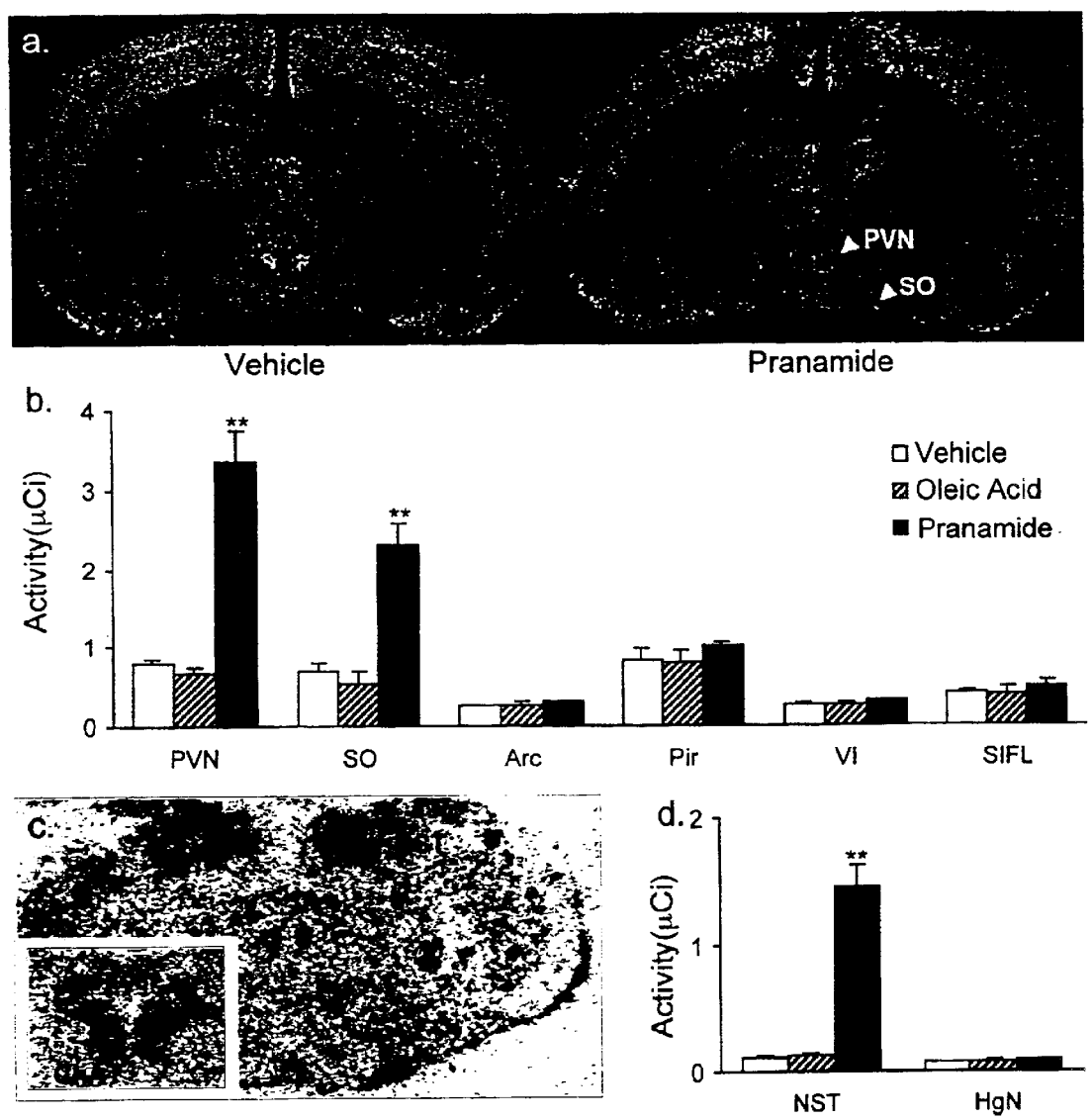
FIG. 7. Oleoylethanolamide/pranamide increases c-fos mRNA expression in discrete brain regions associated with energy homeostasis and feeding behavior: (a) pseudocolor images of film autoradiographs show that oleoylethanolamide (right section) elicits a striking and selective increase in c-fos mRNA labeling in the paraventricular (PVN) and supraoptic (SO) hypothalamic nuclei, as assessed by in situ hybridization. A representative section from a vehicle-treated rat is shown at left. Labeling densities are indicated by color: blue<green<yellow<red. (b) quantification of c-fos cRNA labeling in forebrain regions [PVN, SO, arcuate (Arc), layer II piriform cortex (pir), ventrolateral thalamas (VI) and SI forelimb cortex (S 1FL)] of rats treated with vehicle, oleoylethanolamide and oleic acid; (c) film autoradiogram showing elevated $^{35}$S c-fos mRNA expression in the nucleus of the solitary tract (NST) in an oleoylethanolamide-treated rat; Inset, c-fos cRNA labeling in the NST (shown in red) was identified by its localization relative to adjacent efferent nuclei (hypoglossal and dorsal motor nucleus of the vagus), which express choline acetyl transferase (ChAT) mRNA (shown in purple); (d) oleoylethanolamide increases c-fos mRNA expression in NST but not in the hypoglossal nucleus (HgN). Two asterisks, $P<0.0001$, n=5 per group.

The compounds of the invention may use peripheral sensory inputs to suppress appetite. Peripheral sensory inputs related to appetite suppression recruit several CNS structures, which include the nucleus of the solitary tract (NST) in the brainstem and the arcuate and paraventricular (PVN) nuclei in the hypothalamus (Schwartz et al., *Nature,* 404:661–671 (2000)). To identify the brain pathways engaged during OEA-induced hypophagia, mRNA levels for the activity regulated gene c-fos (Curran et al., *Oncogene,* 2:79–84 (1987)) were mapped by in situ hybridization after systemic administration of OEA, oleic acid or vehicle. When compared to controls, OEA (10 mg per kg, i.p.) evoked a highly localized increase in c-fos mRNA levels in the PVN, supraoptic nucleus (FIG. 7a) and NST (FIG. 7c). This enhancement was specific to these areas, insofar as c-fos expression in other brain regions was not significantly affected by OEA treatment (FIGS. 7b,d). The finding that OEA stimulates c-fos mRNA expression in the NST (which processes vagal sensory inputs to the CNS) and the PVN (a primary site for the orchestration of central catabolic signals) (Schwartz et al., *Nature,* 404:661–671 (2000)), is consistent with a physiological role for this lipid as a peripheral mediator of anorexia.

It is possible that OEA reduced eating by inducing a non-specific state of behavioral suppression. If this is the case, OEA should cause conditioned taste aversion, which can be readily provoked in rats by a number of noxious substances (Green et al., *Science,* 173:749–751 (1971)), including lithium chloride (FIG. 4c). However, a maximal dose of OEA (20 mg per kg, i.p.) had little effect in this assay (FIG. 4c), suggesting that the compound may not be aversive. Several additional observations support the behavioral specificity of OEA. OEA did not alter water intake, body temperature, pain threshold (FIGS. 4d–f), or activity of the hypothalamus-pituitary-adrenal (HPA) axis (Table 3). Moreover, OEA did not produce anxiety-like symptoms (FIG. 4g) and, though it reduced motor activity and operant responses for food, it did so at a dose that was substantially higher than those required to produce hypophagia (FIG. 4h–i). This pharmacological profile differentiates OEA from other appetite suppressants such as amphetamine and glucagon-like peptide 1 (whose effects often include aversion, hyperactivity, anxiety and activation of the HPA axis) and from the endogenous cannabinoid anandamide (which stimulates food intake in partially satiated animals, increases pain threshold, decreases body temperature and activates the HPA axis) (Pertwee, R. G., *Exp. Opin. Invest. Drugs,* 9:1553–1571 (2000)).

TABLE 3

Effects of OEA on plasma hormone levels.

| | B | PRL | LH |
|---|---|---|---|
| vehicle | 212 ± 24 | 10.8 ± 2.7 | 5.3 ± 0.9 |
| prana 20 | 280 ± 61 | 8.2 ± 3.2 | 6.2 ± 1.5 |

In Table 2, plasma corticosterone (B), prolactin (PRL) and luteinizing hormone (LH) levels were measured by radioimmunoassay in plasma samples collected 60 min after injection of vehicle or pranamide (prana, in mg per kg, i.p.) and are expressed in ng per ml. n = 6–9 per group.

OEA elicits hypophagia at physiologically relevant doses. 1 hr after administration of a half-maximally effective dose (5 mg per kg, i.p.), circulating OEA levels (16.1±2.6 pmol per ml) were significantly higher than baseline (10.1±1.1; $P<0.05$, Student's t test; n=5), but below those measured in 18-h food-deprived animals (FIG. 1a). Thus, the concentrations reached by OEA in blood during starvation can be sufficient to elicit notable behavioral responses.

Example 8

Identifying Body Fat Reducing Compounds of the Invention

The following example demonstrates how to identify appetite suppressors using OEA as a positive control. In particular, the synthesis of OEA, the measurement of body fat reduction and fatty acid oxidation are discussed. Synthesis of OEA.

Oleylchloride is purchased from Nu-Check Prep (Elysian, Minn.) or prepared following standard procedures. Oleylchloride is dissolved in dichloromethane (10 mg/ml) and allowed to react with five equivalents of ethanolamine for 15 min. at 0–4° C. The reaction is stopped by the addition of purified water. After vigorous stirring and phase separation, the upper aqueous phase is discarded and the organic phase is washed twice with water to remove non-reacted ethanolamine. The resulting OEA is concentrated to dryness under a $N_2$ stream, reconstituted in chloroform at 20 mM, and stored at −20° C. until use.

Measuring Body Fat Reduction Induced by Candidate Compounds

The ability of a compound to reduce body fat can be evaluated by a number of methods. For example, appropriate amounts OEA and/or candidate compounds are administered to rats via intraperitoneal injection. The OEA and candidate compounds can be formulated in 70% DMSO in sterile saline, 5% Tween 80/5% propylenglycol in sterile saline, or 10% Tween 80/10% ethanol/80% saline. Five mg per kg of OEA can be used as the positive control. Amounts of candidate compounds administered may range, for instance, from 1–25 mg per kg. Typically 1, 2, 5, 10, 15, and 20 mg per kg doses of each candidate compound can be administered to different sets of rats to determine which dose is optimal. Injections may be given 30 minutes before the animals' principal meal for 7–14 days.

The effect of the candidate compound on total body fat can be determined by taking direct measurements of the rat's body fat using skin fold calipers. Skin on the rats' backs, abdomen, chest, front and rear legs can be pinched with calipers to obtain measurements before administration of OEA and/or candidate compounds and every 48 hours during and after administration of OEA and/or candidate compounds. Differences in measurements in at least two of the pinched sites reflect the change in the rat's total body fat.

Measuring Fatty Acid Oxidation Induced by Candidate Compounds

Compounds can also be assayed for their effect on fatty acid metabolism. The effect of the candidate compound on fatty acid metabolism can be measured by measurements of fatty acid oxidation in primary cultures of liver cells. Hepatocytes may be used to determine the rate of oleate oxidation to ketone bodies and carbon dioxide. Such cells can be isolated from adult rat liver by enzymatic digestion as described by Beynen et al. in *Diabetes* 28:828 (1979). Cells typically are cultured in suspension and incubated in Krebs-Henseleit's bicarbonate medium supplemented with bovine serum albumin and glucose as described by Guzmán & Geelen, *Biochem. J.* 287:487(1992). The protein concentration of the cultured cells can be determined and cells seeded in 2 ml media so that 4–6 mg protein per ml is present in the reaction mixture. Cells can be incubated for 10 minutes at 37° C. with [$^{14}$C]-oleic acid (Arnersham), in the presence or absence of 10 μM OEA, reactions may be stopped with 200 μl 2M perchloric acid and acid-soluble products extracted with chloroform/methanol/water (5:1:1, vol:vol:vol). The aqueous phase can be removed and washed twice more. Protein concentration can be determined using a Lowry assay. The rate of oleate conversion into ketone bodies may be expressed as rnmol of oleate oxidized per hour per mg protein and may be determined using liquid scintillation counting. Accordingly, OEA enhances oleate oxidation by 21+−6% (n=4, p<0.01 vs. control incubations by the Student t test).

Example 9

Effect of OEA on Fatty Acid Metabolism

Figure 8:
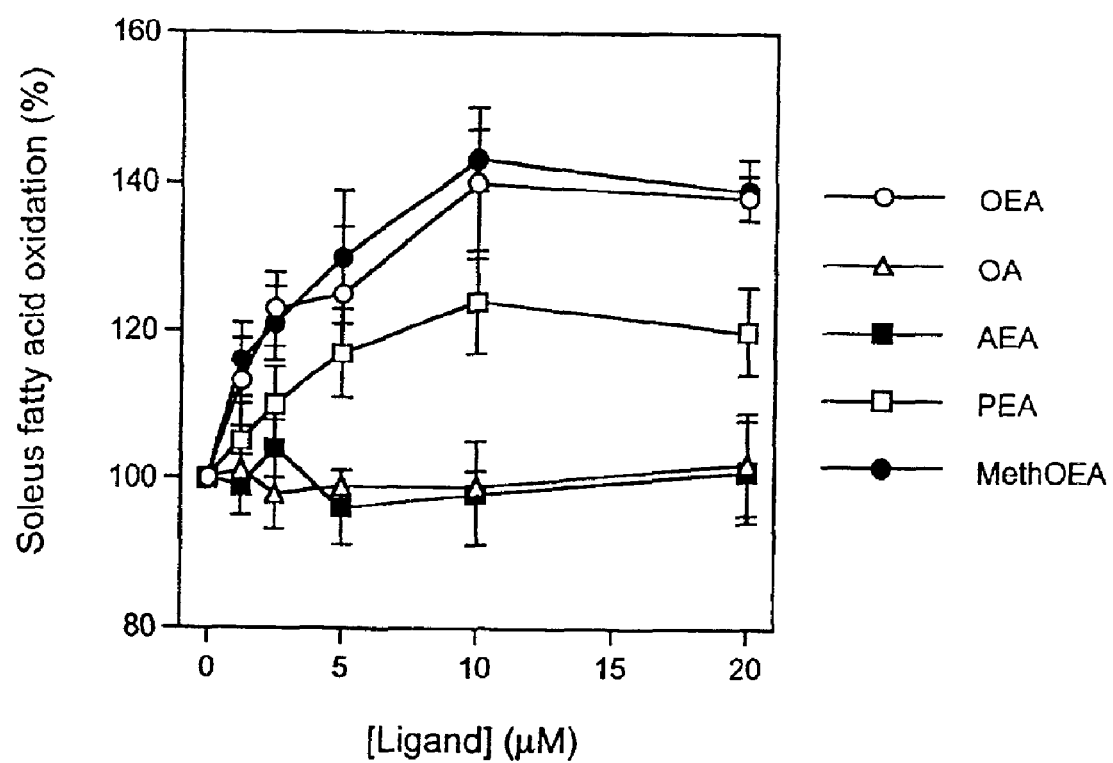
FIG. 8. The effects of OEA, Oleic acid (OA), AEA, PEA, and methyl-OEA on fatty acid oxidation in soleus muscle.

Oleoylethanolamide (OEA) decreases body weight not only by suppressing appetite, but also by possibly enhancing body fat catabolism. The effects of OEA on fatty acid oxidation in major body-fat burning tissues (soleus muscle, liver, cultured cardiac myocytes and astrocytes) was examined. OEA significantly stimulates fatty acid oxidation in primary cultures of liver, skeletal muscle (soleus) and heart cells, whereas it has no effect in brain-derived astroglial cell cultures. In addition, OEA induces a significant mobilization of triacylglycerol stores from primary white adipose tissue cells. Table 4 details the methods and effects of OEA on fatty acid oxidation in these cells. Structure-activity relationship experiments provide evidence that the effect of OEA on skeletal muscle fatty acid oxidation is specific (FIG. 8). Thus, the effects of OEA are mimicked by the hydrolysis-resistant homologue methyl-OEA and -only partially- by palmitylethanolamide (PEA), but not by arachidonylethanolamide (AEA) or oleic acid (OA). In short, these results show that lipid oxidation and mobilization are enhanced by OEA, and that the effects of OEA are restricted to peripheral sites.

TABLE 4

| Cell/tissue | Hepatocyte | Soleus muscle | Cardiomyocyte | Astrocyte | Adipocyte |
|---|---|---|---|---|---|
| Origin | Adult rat liver | Adult rat hind limb | Newborn rat heart | Newborn rat brain cortex | Adult rat epididymus |
| Isolation procedure | Enzymatic digestion (Beynen et al., 1979) | Dissection (Chiasson, 1980) | Enzymatic digestion (Flink et al., 1992) | Enzymatic digestion (McCarthy & De Vellis, 1980) | Enzymatic digestion (Rodbell, 1964) |
| Type of culture | Cell suspension | Tissue suspension | Cell monolayer | Cell monolayer | Cell suspension |
| Incubation medium | Krebs-Henseleit bicarbonate plus BSA and glucose (Guzman & Geelen, 1992) | Krebs-Henseleit Hepes plus BSA and glucose (Fruebis et al., 2001) | High-glucose DMEM plus BSA (Wu et al., 2000) | Hams F12/DMEM plus insulin, transferrin, progesterone, putrescine and selenite (Blazquez et al., 1998 | Krebs-Henseleit Hepes plus BSA and glucose (Rodbell, 1965) |
| Metabolic parameter | [$^{14}$C]oleate oxidation to | [$^{14}$C]oleate oxidation to | [$^{14}$C]oleate oxidation to | [$^{14}$C]oleate oxidation to | Lypolysis (glycerol |

TABLE 4-continued

| Cell/tissue | Hepatocyte | Soleus muscle | Cardiomyocyte | Astrocyte | Adipocyte |
|---|---|---|---|---|---|
| | ketone bodies (Guzman & Geelen, 1992) | $CO_2$ (Fruebis et al., 2001) | $CO_2$ (Blazquez et al., 1998) | ketone bodies (Blazquez et al., 1998) | release) (Serradeil-Le Gal et al., 2000) |
| Incubation time (min) | 10 | 30 | 30 | 30 | 30 |
| Stimulatory effect of 10 µM OEA (%) | 21 ± 6 (n = 4) | 36 ± 10 (n = 4) | 37 ± 9 (n = 3) | 2 ± 6 (n = 3) | 38 ± 16 (n = 3) |
| Statistical significance vs. control | $P < 0.01$ | $P < 0.01$ | $P < 0.01$ | Non significant | $P < 0.01$ |

References cited: Beynen AC et al., Diabetes 28: 828–835 (1979); Blazquez C et al., J Neurochem 71: 1597–1606 (1998); Chiasson RB "Laboratory Anatomy of the White Rat" WCB, Dubuque, Iowa (1980); Funk IL et al., J Biol Chem 267: 9917–9924 (1992); Fruebis J et al., Proc Natl Acad Sci USA 98: 2005–2010 (2001); Guzman M et al., Biochem J 287: 487–492 (1992); McCarthy KD et al., J Cell Biol 85: 890–902 (1980);Rodbell M J Biol Chem 239: 375–380 (1964); Rodbell M Ann NY Acad Sci 131: 302–314 (1965); Serradiel-Le Gal C et al., FEBS Left 475: 150–156 (2000); Wu W et al., J Biol Chem 275: 40133–40119 (2000).

Example 10

Role of Endogenous OEA in the Intestines

The impact of feeding on intestinal OEA biosynthesis was studied. High performance liquid chromatography/mass spectrometry analyses revealed that small intestinal tissue from free-feeding rats contains substantial amounts of OEA (354±86 pmol per g, n=3). Intestinal OEA levels were markedly decreased after food deprivation, but returned to baseline after refeeding. By contrast, no such changes were observed in stomach (in pmol per g; control, 210±20; starvation, 238±84; starvation/refeeding, 239±60, n=3). Variations in intestinal OEA levels were accompanied by parallel alterations in NAT activity, which participates in OEA formation, but not in fatty acid amide hydrolase activity, which catalyzes OEA hydrolysis. These findings suggest that starvation and feeding reciprocally regulate OEA biosynthesis in small intestine. In agreement with an intra-abdominal source of OEA, plasma OEA levels in starved rats were found to be higher in portal than in caval blood (in pmol per ml; porta, 14.6±1.8; cava, 10.3±2.8; n=5). The contribution of other intra-abdominal tissues to OEA formation cannot be excluded at present. These results suggest many interventions to utilize the OEA systems in feeding behavior. According to this model, food intake may stimulate NAT activity enhancing OEA biosynthesis in the small intestine and possibly other intra-abdominal tissues. Newly produced OEA may activate local, sensory fibers, which may in turn inhibit feeding by engaging brain structures such as the NST and PVN.

Our results reveal an unexpected role for OEA in the peripheral regulation of feeding, and provide a framework to develop novel medicines for reducing body weight or body fat, for preventing body weight gain or body fat increase, for suppressing appetite or reducing food seeking behavior, or food intake, and for the treating eating disorders, overweight, or obesity. These medicines would include not only OEA analogues and homologues but also agents which controlling OEA levels by acting upon the OEA formation and hydrolyzing systems and enzymes as disclosed above.

All publications and patent applications cited in this specification are herein incorporated by reference to the extent not inconsistent with the present disclosure as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of reducing food intake in a mammal in need thereof, said method comprising administering to said mammal a fatty acid alkanolamide in an effective amount to reduce food intake in said mammal, wherein the fatty acid alkanolamide is a compound of the formula:

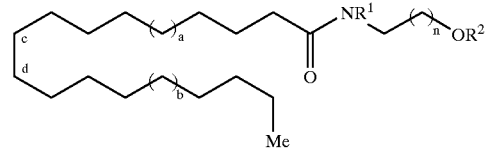

or a pharmaceutically acceptable salt thereof, wherein n is an integer from 1 to 5; a and b are each an integer wherein the sum of a and b is from 0 to 4; and $R^1$ is hydrogen and $R^2$ is selected from the group consisting of hydrogen, unsubstituted ($C_1$–$C_6$) alkyl, and unsubstituted ($C_2$–$C_6$) acyl, and wherein optionally up to four hydrogen atoms of the fatty acid portion and alkanolamide portion of the formula are substituted by methyl or a double bond joining adjacent carbons of the formula, and additionally the bond between carbons c and d may be unsaturated or saturated.

2. The method according to claim 1, wherein the fatty acid alkanolamide is oleoylethanolamide.

3. The method of claim 1, wherein n is 1.

4. The method of claim 1, wherein the fatty acid portion is monounsaturated.

5. The method of claim 1, wherein the administering is via a dermal patch.

6. The method of claim 4, wherein the fatty acid portion is oleic acid.

7. The method of claim 3, wherein the fatty acid portion is selected from the group consisting of elaidic acid, palmitoleic acid, palmitic acid, linoleic acid, aipha-linolenic acid, and gamma-linolenic acid.

8. The method of claim 3, wherein n is 1 and $R^2$ is a lower ($C_1$–$C_3$) alkyl.

9. The method of claim 3, wherein n is 1 and $R^2$ is straight or branched ($C_2$–$C_6$) acyl.

10. The method according to claim 1, wherein the mnammal is human.

11. The method according to claim 1, wherein the fatty acid alkanolamide is palmitoylethanolamide.

12. The method according to claim 1, wherein said fatty acid alkanolamide is administered with a pharmaceutically acceptable carrier by an oral, rectal, topical, or parenteral route.

13. The method of claim 1, wherein a dose of the fatty acid alkanolamide in an amount from about 10 mg to 1000 mg of the fatty acid alkanolamide is administered.

14. The method of claim 1, wherein a dose of about 1 mg to 100 mg of the fatty acid alkanolaniide is administered.

15. The method of claim 1, wherein a dose of about 100 mg to 500 mg of the fatty acid alkanolamide is administered.

16. The method of claim 1, wherein the fatty acid alkanolamide is administered in a unit dose format.

17. The method of claim 1, wherein the fatty acid alkanolamide is administered orally.

18. The method of claim 1, wherein the fatty acid alkanolamide is orally administered in a tablet, pill, or capsule form.

19. The method of claim 1, wherein the administering is topical.

20. A method of reducing food intake in a mammal in need thereof, said method comprising administering to said mammal in an effective amount to reduce body fat or body weight, a compound of the formula:

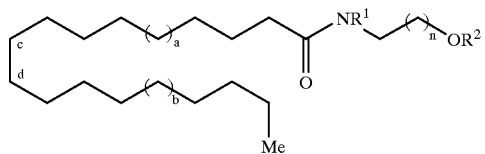

or a pharmaceutically acceptable salt thereof, wherein n is an integer from 1 to 5; a and b are each an integer wherein the sum of a and b is from 0 to 4; and $R^1$ is hydrogen and $R^2$ is selected from the group consisting of hydrogen, unsubstituted ($C_1$–$C_6$) alkyl, and unsubstituted ($C_2$–$C_6$) acyl, and wherein, optionally, up to four hydrogen atoms of the fatty acid portion and alkanolamide portion of the formula are substituted by methyl or a double bond joining adjacent carbons of the formula, and additionally the bond between carbons c and d may he unsaturated or saturated.

21. The method of claim 1, wherein one of the hydrogen atoms of the fatty acid portion and alkanolamide portion of the compound is substituted by methyl.

22. The method of claim 21, wherein the compound is selected from the group consisting of $(R)^{1'}$-methyloleoylethanolamide, $(S)^{1'}$-methyloleoylethanolamide, $(R)^{2'}$-methyloleoylethanolamide, $(S)^{2'}$-methyloleoylethanolamide, $(R)^{1}$-methyloleoylethanolamide, (S)1-methyloleoylethanolamide and the pharmaceutically acceptable salts thereof.

23. The method of claim 1, wherein $R^2$ is —C(O)CH$_2$CH$_3$, —C(O)CH$_2$CH$_2$CH$_3$, or —C(O)CH$_3$.

24. The method of claim 1, wherein n is 1 and $R^2$ is hydrogen.

25. The method of claim 7, wherein n is 1 and $R^2$ is hydrogen.

26. The method of claim 2, wherein the mammal is human.

27. The method of claim 1, wherein $R^2$ is H.

28. The method of claim 1, wherein the fatty acid alkanolamide is elaidylethanolamide.

29. The method of claim 1, wherein there is a double bond between carbons c and d.

30. The method of claim 1, wherein a=1, b=1.

31. The method of claim 1, wherein a=1, b=1, and n=1.

32. The method of claim 29, wherein the stereochemistry of the compound about the double bond is E.

33. The method of claim 29, wherein the stereochemistry of the compound about the double bond is Z.

34. The method of claim 20, wherein there is a double bond between carbons c and d.

* * * * *